(12) United States Patent
Alami et al.

(10) Patent No.: US 12,371,417 B2
(45) Date of Patent: Jul. 29, 2025

(54) COMPOUNDS WITH TUBULIN POLYMERISATION INHIBITORY ACTIVITY AND IMMUNOMODULATORY PROPERTIES

(71) Applicants: UNIVERSITE PARIS-SACLAY, Saint Aubin (FR); CENTRE NATIONAL DE LA RECHERCHE SCIENTIFIQUE (CNRS), Paris (FR); INSTITUT GUSTAVE-ROUSSY, Villejuif (FR); INSTITUT NATIONAL DE LA SANTE ET DE LA RECHERCHE MEDICALE (INSERM), Paris (FR)

(72) Inventors: Mouad Alami, Bussy Saint Georges (FR); Olivier Provot, Sartrouville (FR); Abdallah Hamze, Massy (FR); Ilhem Khelifi, Le Raincy (FR); Timothée Naret, Orchamps (FR); Sébastien Apcher, Franconville (FR); Romain Darrigrand, Ivry sur Seine (FR)

(73) Assignees: UNIVERSITE PARIS-SACLAY, Saint Aubin (FR); CENTRE NATIONAL DE LA RECHERCHE SCIENTIFIQUE (CNES), Paris (FR); INSTITUT GUSTAVE ROUSSY, Villejuif (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 18/117,847

(22) Filed: Mar. 6, 2023

(65) Prior Publication Data
US 2023/0203005 A1 Jun. 29, 2023

Related U.S. Application Data

(62) Division of application No. 17/050,772, filed as application No. PCT/FR2019/050982 on Apr. 26, 2019, now Pat. No. 11,634,405.

(30) Foreign Application Priority Data

Apr. 27, 2018 (FR) .................................. 1853709

(51) Int. Cl.
| | | |
|---|---|---|
| A61K 31/4725 | (2006.01) | |
| A61P 35/00 | (2006.01) | |
| C07D 401/12 | (2006.01) | |
| C07D 403/12 | (2006.01) | |

(52) U.S. Cl.
CPC ........ *C07D 401/12* (2013.01); *A61K 31/4725* (2013.01); *A61P 35/00* (2018.01); *C07D 403/12* (2013.01)

(58) Field of Classification Search
CPC .................................................. A61K 31/4725
See application file for complete search history.

(56) References Cited

U.S. PATENT DOCUMENTS

2010/0129471 A1  5/2010  Alami et al.

FOREIGN PATENT DOCUMENTS

| EP | 0602851 A1 | 6/1994 |
|---|---|---|
| WO | WO 00/47212 A1 | 8/2000 |
| WO | WO 2005/046698 A1 | 5/2005 |
| WO | WO 2005/063739 A1 | 7/2005 |
| WO | WO 2007/034143 A1 | 3/2007 |
| WO | WO 2008/122620 A1 | 10/2008 |

OTHER PUBLICATIONS

French Search Report for French Application No. 1853709, dated Oct. 1, 2018.
Hu et al., "Design, Synthesis, and Biological Evaluation of Novel Quinazoline Derivatives as Anti-Inflammatory Agents against Lipopolysaccharide-induced Acute Lung Injury in Rats," Chem. Biol. Drug. Des., vol. 85, 2015, pp. 672-684.
International Search Report and Written Opinion of the International Searching Authority (Forms PCT/ISA/220, PCT/ISA/210 and PCT/ISA/237) for International Application No. PCT/FR2019/050982 dated Jul. 26, 2019.
Khelifi et al. (European Journal of Medicinal Chemistry, 2019, 168, pp. 176-188).
Kidwai et al., "Cancer Chemotherapy and Heterocyclic Compounds," Current Medicinal Chemistry, vol. 9, No. 12, 2002, pp. 1209-1228.
Kumar et al., "Palladium-catalyzed regioselective aerobic oxidative cyclization via C—H activation in chloroquine analogues: synthesis and cytoxic study," Monatsh Chem, vol. 146, 2015, pp. 2127-2134.

(Continued)

*Primary Examiner* — Brian E McDowell
(74) *Attorney, Agent, or Firm* — Birch, Stewart, Kolasch & Birch, LLP

(57) ABSTRACT

The present invention relates to the Compound of following formula (I):

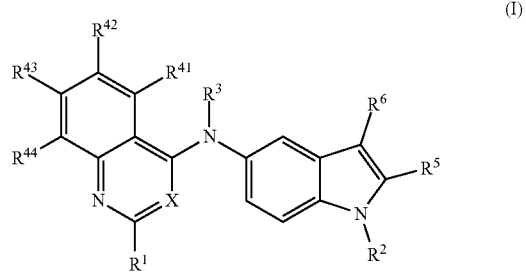

or a pharmaceutically acceptable salt thereof.
The present invention also relates to a pharmaceutical composition containing such a compound and a method for preparing such a compound.

16 Claims, 4 Drawing Sheets

(56) References Cited

OTHER PUBLICATIONS

Mahal et al., "Effects of the Tumor-Vasculature-Disrupting Agent Verubulin and Two Heteroaryl Analogues on Cancer Cells, Endothelial Cells, and Blood Vessels," ChemMedChem, vol. 9, 2014, pp. 847-854.

COMPOUNDS WITH TUBULIN POLYMERISATION INHIBITORY ACTIVITY AND IMMUNOMODULATORY PROPERTIES

CROSS-REFERENCE TO RELATED APPLICATIONS

This application is a Divisional of copending U.S. application Ser. No. 17/050,772, filed on Oct. 26, 2020, which was filed as PCT International Application No. PCT/FR2019/050982 on Apr. 26, 2019, which claims the benefit under 35 U.S.C. § 119(a) to Patent Application No. 1853709, filed in France on Apr. 27, 2018, all of which are hereby expressly incorporated by reference into the present application.

FIELD OF THE INVENTION

The present invention relates to compounds acting as antivascular agents through tubulin polymerisation inhibition and/or having immunomodulatory properties, the method of preparation thereof as well as the use thereof in the treatment of cancer.

PRIOR ART

Cancer is the leading cause of mortality in men aged below 65 years, the second cause in women. More than 2 million new cases are diagnosed annually in Europe. The number of deaths due to cancer in France was estimated at 150,000 in 2015. The impact of cancer on society thus remains considerable.

The major types of treatments against cancer are: surgery, radiotherapy, so-called conventional chemotherapy (involving cytotoxic agents), targeted therapies (specifically targeting certain mechanisms involved in cell regulation and growth), hormonotherapy (suitable in the case of cancers sensitive to the action of hormones naturally produced by the organism), immunotherapy (aiming to stimulate the immune system of the sick person against tumoral cells).

Conventional chemotherapy involving cytotoxic agents, alone or associated with surgery or radiotherapy, occupies a major place. However, the treatments are frequently accompanied by undesirable effects through lack of selectivity. In addition, multi-resistance, the main mechanism through which numerous cancers escape treatments, is an important factor in the failure of numerous chemotherapies.

The recent progress made in the treatment of cancers is linked to the arrival of targeted therapies. In this context, normalising, destroying or deregulating tumour vascularisation are the objectives of a new targeted therapeutic strategy which is generating much hope. This strategy, exclusively targeting endothelial cells genetically more stable than cancerous cells, decreases the risk of resistance to the treatment. Fosbretabulin, the leading antivascular agent, received in 2016 the status of orphan drug in the United States and in Europe for the treatment of neuro-endocrine tumours (NETs) and multiform glioblastoma (MGB).

Despite all the interest of targeted therapies, treatments aimed at a single target have shown limited results on account of the great biological diversity of cancers and the appearance of resistance phenomena. The combination of several active principles (or polychemotherapy) having different action mechanisms and targeting the most critical alterations of this disease seem judicious, providing that the toxicity of each active principle taken separately is not cumulated. Avenues for development are now linked to the use of dual molecules which inhibit or modulate several targets simultaneously. Tyrosine kinase inhibitors (TKI) represent a good example of this concept, capable of blocking the signalling of VEGF, PDGF receptors and other membranal and/or cytoplasmic kinases. The advantages of this strategy are multiple: (i) better effectiveness on account of the synergism of the simultaneous effect on several targets, (ii) a single metabolization rate, simplifying the pharmacokinetic and pharmacodynamic parameters, (iii) a lowering or even an absence of interaction between the various active principles administered, etc.

Unlike targeted therapies, immunotherapy does not aim to directly destroy cancerous cells. It targets the immune system in order to reinforce and stimulate the sick person's own defences against cancerous cells. This approach has enabled the placing on the market of so-called "immunomodulatory" monoclonal antibodies such as anti-CTLA-4 (ipilimumab/YERVOY®, metastatic melanoma) or anti-PD-1/PD-L1 (pembrolizumab/KEYTRUDA®, nivolumab/OPDIVA®, renal cancer, lung cancer, etc.). Immunomodulators may also be small chemical molecules acting in a targeted manner against an actor of the immune response. To date, only thalidomide and derivatives thereof have been described as immunomodulatory molecules (multiple myeloma). If these active principles are used clinically, the fact remains that they are accompanied by several drawbacks of which mainly a teratogenic effect, and a higher risk of secondary cancers (acute myeloblastic leukaemia and myelodysplastic syndromes) considerably limiting the use thereof. Consequently, the search for small immunomodulatory molecules is a field that is generating much hope.

An immuno-therapeutic strategy against cancer could consist in targeting the stimulation of cytotoxic CD8 T lymphocytes. CD8 T lymphocytes recognise certain antigens, small endogen peptides of eight to ten amino acids primed in a class I major histocompatibility complex (MHC-I) molecule. Alterations in the components of the machinery of presentation by MHC-I have been demonstrated in numerous types of cancers, leading to a decrease or a loss of antigen presentation and thus favouring tumour escape. Increasing antigen presentation within tumours by means of small molecules could make it possible to improve the visibility of tumoral cells faced with CD8 T lymphocytes. These small molecules could then have an immunomodulatory activity by making the tumoral cells more visible to CD8 T lymphocytes.

The combination of the two therapeutic approaches, one targeting tumour vascularisation and the other the immune system, constitutes the rational of this patent application with the identification of a new class of "multi-target" antitumoral compounds acting both as antivascular and as immunomodulator.

Combretastatin A-4 (CA-4), a molecule of natural origin, is recognised as an antivascular agent on account of its ability to interact with the tubulin of endothelial cells activated by growth factors of which the vascular endothelial growth factor (VEGF) is the essential actor. It selectively destroys the vessels irrigating tumours, thus inducing important intra-tumoral necrosis. Fosbretabulin, prodrug of combretastatin A-4, has received the status of orphan drug in the United States and in Europe for cancers of the thyroid and chronic myeloid leukaemias. Other clinical trials are underway, in combination with other agents such as bevacizumab against resistant ovarian cancer. Although effective in therapy, combretastatin A-4 is burdened with several handicaps of which chemical instability, imputable to the isomerisation of the double bond Z leading to the inactive isomer E, imposing conservation at low temperature and protected from light.

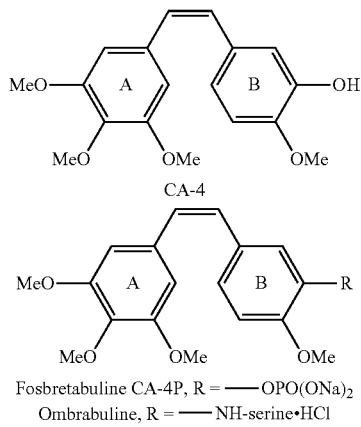

CA-4

Fosbretabuline CA-4P, R = —OPO(ONa)$_2$
Ombrabuline, R = —NH-serine·HCl

A means of getting round the recurrent problem of instability of the double bond Z of CA-4 has been developed in the application WO 2008/122620. Isocombretastatin A-4 (isoCA-4), and isoaminocombretastatin A-4 (isoNH$_2$CA-4) have been identified as two leaders of which the biological profile (cytotoxicity, tubulin polymerisation inhibition, induction of apoptosis, etc.) is rigorously identical to that of the natural molecule, without however having the risk of isomerisation of the double bond. These molecules are particularly stable and do not metabolise in the presence of hepatocytes.

Continuing their structure-activity relationship study work, the inventors have discovered in a surprising manner compounds having not only cytotoxic and tubulin polymerisation inhibition properties, but also immunomodulatory properties.

Furthermore, the antiproliferative activity of the compounds according to the invention is observed at very low concentrations varying from the picomolar to the nanomolar.

Similarly, the immunomodulatory activity of the compounds according to the invention is observed at very low nanomolar concentrations.

SUMMARY OF THE INVENTION

The present invention relates to compounds of following formula (I):

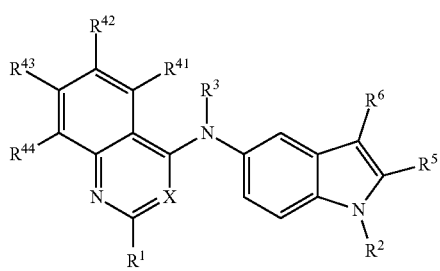

in which:
X represents a —CH— group or a nitrogen atom,
$R^1$ represents a hydrogen atom, a halogen atom, preferably a chlorine atom, a $(C_1-C_6)$alkyl group, preferably a methyl group, a —CN group or a —CF$_3$ group,
$R^2$ represents a hydrogen atom, a $(C_1-C_6)$alkyl group, an aryl-$(C_1-C_6)$alkyl group, preferably a benzyl, or a —COR$^{21}$ group with $R^{21}$ representing a $(C_1-C_6)$alkyl group or an aryl group,
$R^3$ represents a hydrogen atom, a $(C_1-C_6)$alkyl group, preferably a methyl group, an aryl-$(C_1-C_6)$alkyl group or a —COR$^{31}$ group with $R^{31}$ representing a $(C_1-C_6)$alkyl group, preferably a $(C_1-C_6)$alkyl group, preferably a methyl group, an aryl-$(C_1-C_6)$alkyl group or a —COR$^{31}$ group with $R^{31}$ representing a $(C_1-C_6)$alkyl group or an aryl group,
$R^{41}$, $R^{42}$, $R^{43}$ and $R^{44}$ represent independently of each other a hydrogen atom; a halogen atom; —OR$^{45}$; —SR$^{45}$; —NR$^{45}R^{46}$; —NO$_2$; or a $(C_1-C_6)$alkyl group optionally substituted by one or more substituents selected from among a halogen atom, —OR$^{45}$, —SR$^{45}$, —NR$^{45}R^{46}$ and —NO$_2$, with $R^{45}$ and $R^{46}$ representing independently of each other a hydrogen atom, a $(C_1-C_6)$alkyl group, a —CF$_3$ group or a —COR$^{47}$ group with $R^{47}$ representing a $(C_1-C_6)$alkyl group or an aryl group,
$R^5$ and $R^6$ represent a hydrogen atom or form together a —CR$^{51}$=CR$^{52}$—CR$^{53}$=CR$^{54}$— chain with $R^{51}$, $R^{52}$, $R^{53}$ and $R^{54}$ representing independently of each other a hydrogen atom; a halogen atom; —OR$^{55}$; —SR$^{55}$; —NR$^{55}R^{56}$; —NO$_2$; or a $(C_1-C_6)$alkyl group optionally substituted by one or more substituents selected from among a halogen atom, —OR$^{55}$, —SR$^{55}$, —NR$^{55}R^{56}$ and —NO$_2$, with $R^{55}$ and $R^{56}$ representing independently of each other a hydrogen atom, a $(C_1-C_6)$alkyl group, a —CF$_3$ group or a —COR$^{57}$ group with $R^{57}$ representing a $(C_1-C_6)$alkyl group or an aryl group.

or a pharmaceutically acceptable salt thereof.

The present invention also relates to a compound (I) such as described above or a pharmaceutically acceptable salt thereof for the use thereof as a drug, notably intended to treat cancer, while acting in particular through tubulin polymerisation inhibition and/or through immunomodulation.

The present invention also relates to a pharmaceutical composition comprising at least one compound (I) such as described above or a pharmaceutically acceptable salt thereof and a pharmaceutically acceptable excipient.

The present invention also relates to a pharmaceutical composition comprising at least one compound (I) such as described above or a pharmaceutically acceptable salt thereof and a pharmaceutically acceptable excipient for the use thereof as a drug, notably intended to treat cancer, while acting in particular through tubulin polymerisation inhibition and/or through immunomodulation.

The present invention also relates to the use of a compound (I) such as described above or a pharmaceutically acceptable salt thereof for the preparation of a drug intended for the treatment of cancer.

The present invention also relates to a method for treating cancer comprising the administration to a patient in need thereof of an effective quantity of a compound (I) such as described above or a pharmaceutically acceptable salt thereof or a pharmaceutical composition such as defined above.

Finally, the present invention relates to a method for preparing a compound (I) such as described above or a pharmaceutically acceptable salt thereof comprising the following steps:
(1) coupling an amine derivative of following formula (II):

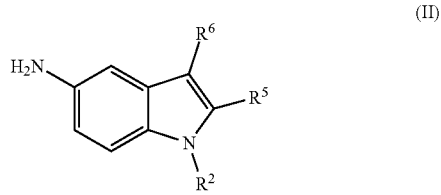

in which $R^2$, $R^5$ and $R^6$ are such as defined above, with a compound of following formula (III):

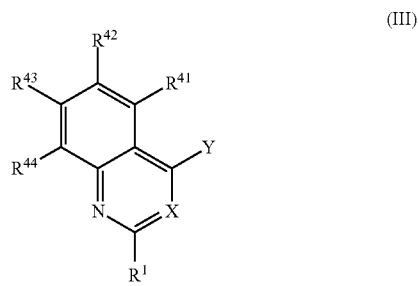

in which Y represents an atom of chlorine, bromine, iodine, a trifluoromethylsulphonate group or a tosyl group and X, $R^1$, $R^{41}$, $R^{42}$, $R^{43}$ and $R^{44}$ are such as defined above, to give a compound of formula (I) such as described above with $R^3$=H,
(2) optionally substituting the $R^3$=H group borne by the amine of the compound of formula (I) obtained at step (1) which precedes to give a compound of formula (I) such as described above with $R^3$ representing a ($C_1$-$C_6$)alkyl group, an aryl-($C_1$-$C_6$)alkyl group or a —$COR^{31}$ group with $R^{31}$ such as defined above, and
(3) optionally salifying of the compound of formula (I) obtained at step (1) or (2) which precedes to give a pharmaceutically acceptable salt of a compound of formula (I) such as defined above.

DEFINITIONS

Figure 1:
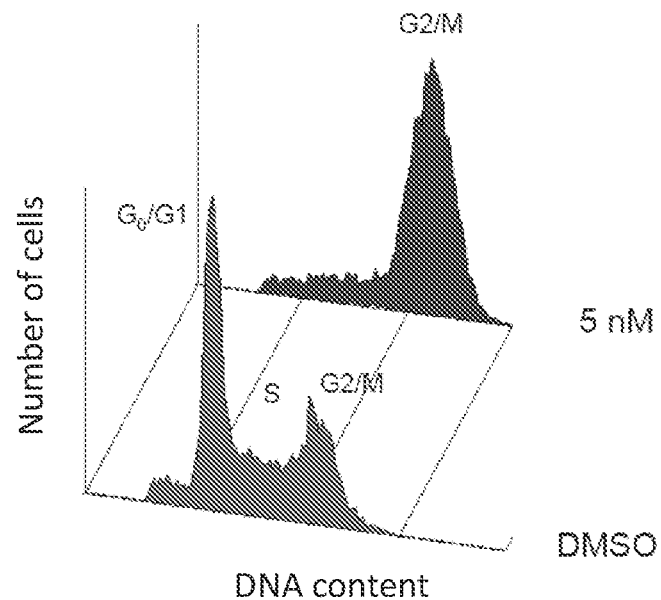
FIG. 1 represents the number of HCT116 cells as a function of their DNA content in the different phases of the cell cycle (G0/G1, S, G2/M) after 24 hours of treatment in the presence of DMSO (control—vehicle alone) or in the presence of compound 1 at a concentration of 5 nM in DMSO.

The term "halogen", such as used in the description of the present invention, designates fluorine, chlorine, bromine and iodine atoms. Advantageously, it will be fluorine, bromine and chlorine and even more advantageously fluorine or chlorine.

The term "($C_1$-$C_6$)alkyl", such as used in the description of the present invention, designates any saturated hydrocarbon group comprising from 1 to 6 carbon atoms, linear or branched, in particular methyl, ethyl, n-propyl, isopropyl, n-butyl, iso-butyl, sec-butyl, tert-butyl, pentyl and hexyl groups.

The term "aryl", such as used in the description of the present invention, designates one or more aromatic rings having from 5 to 10 carbon atoms, being able to be fused together. In particular, the aryl groups may be monocyclic or bicyclic groups, such as for example the phenyl or naphthyl group. Advantageously, the aryl group is a phenyl.

The term "aryl-($C_1$-$C_6$)alkyl", such as used in the description of the present invention, designates an aryl group such as defined above, bound to the remainder of the molecule through a ($C_1$-$C_6$)alkyl chain such as defined above. As an example, the benzyl or instead phenylethyl group may be cited.

The expression "pharmaceutically acceptable", such as used in the description of the present invention, designates what is useful in the preparation of a pharmaceutical composition, which is generally safe, non-toxic and neither biologically or otherwise undesirable and which is acceptable for veterinary use and/or human pharmaceutical use. The expression "pharmaceutically acceptable salts", such as used in the description of the present invention, designates salts of a compound that are pharmaceutically acceptable, as defined here, and which have the desired pharmacological activity of the parent compound.

Such salts comprise:
(1) hydrates and solvates,
(2) acid addition salts formed with inorganic acids such as hydrochloric acid, hydrobromic acid, sulphuric acid, nitric acid, phosphoric acid and similar; or formed with organic acids such as acetic acid, benzenesulphonic acid, benzoic acid, camphorsulphonic acid, citric acid, ethanesulphonic acid, fumaric acid, glucoheptonic acid, gluconic acid, glutamic acid, glycolic acid, hydroxy naphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartric acid, tartric acid, p-toluenesulphonic acid, trimethyl acetic acid, trifluoroacetic acid and similar.
Advantageously, it is hydrochloric acid; or
(3) salts formed when an acid proton present in the parent compound either is replaced by a metal ion, for example an alkali metal ion, an alkaline-earth metal ion; or coordinates with an organic or inorganic base. Acceptable organic bases comprise diethanolamine, ethanolamine, N-methylglucamine, triethanolamine, tromethamine and similar. Acceptable inorganic bases comprise aluminium hydroxide, calcium hydroxide, potassium hydroxide, sodium carbonate and sodium hydroxide. Advantageously, the acid proton is displaced by an Na⁺ ion, notably using sodium hydroxide. The acid addition salts are formed in particular with an amine function or with a pyridine. The base addition salts are formed in particular with a carboxylic acid (—COOH), phosphate (—OP(O)(OH)$_2$) or sulphate (—OSO$_3$H) function. The term "stereoisomers", such as used in the description of the present invention, designates diastereoisomers or enantiomers. They are thus configuration isomers. Stereoisomers which are not mirror images of each other are thus designated "diastereoisomers", and stereoisomers which are mirror images of each other but not superimposable are designated "enantiomers", also called "optical isomers". A carbon atom bound to four non-identical substituents is called a "chiral centre". When a molecule has such a chiral centre, it is called chiral and has two enantiomer forms. When a molecule has several chiral centres, then it will have several diastereoisomer and enantiomer forms. An equimolar mixture of two enantiomers is called a racemic mixture.

The expression "compounds of the present invention" or "compounds of formula (I)" or "compound (I)" such as used in the present description designates compounds of formula (I), but also sub-formulas (Ia) and (Ib) such as defined in a detailed manner below, and pharmaceutically acceptable salts thereof.

DETAILED DESCRIPTION OF THE INVENTION

Compounds of Formula (I) According to the Invention

The invention relates to compounds of formula (I) such as defined above or a pharmaceutically acceptable salt thereof.

According to a first embodiment X represents a nitrogen.

According to a second embodiment X represents a CH group.

Advantageously, in these two embodiments, according to a first alternative, $R^3$ represents a (C$_1$-C$_6$)alkyl group, preferably a methyl group.

In particular, in these two embodiments and optionally according to the first alternative, according to a second alternative, $R^2$ represents a (C$_1$-C$_6$)alkyl group, preferably a methyl group, or an aryl-(C$_1$-C$_6$)alkyl group, preferably a benzyl group. More specifically, $R^2$ represents a (C$_1$-C$_6$)alkyl group, preferably a methyl group.

Preferably, in these two embodiments and the alternatives thereof, $R^{41}$, $R^{42}$, $R^{43}$ and $R^{44}$ represent independently of each other a hydrogen atom, a halogen atom, —OR$^{45}$, —SR$^{45}$, —NR$^{45}$R$^{46}$ or —NO$_2$ with R$^{45}$ and R$^{46}$ representing independently of each other a hydrogen atom, a CF$_3$ group or a (C$_1$-C$_6$)alkyl group, notably a hydrogen atom or a (C$_1$-C$_6$)alkyl group. In particular, $R^{41}$, $R^{42}$, $R^{43}$ and $R^{44}$ represent independently of each other a hydrogen atom, —OR$^{45}$, —NR$^{45}$R$^{46}$ or —NO$_2$ with R$^{45}$ and R$^{46}$ representing independently of each other a hydrogen atom, a CF$_3$ group or a (C$_1$-C$_6$)alkyl group, notably a hydrogen atom, or a (C$_1$-C$_6$)alkyl group.

According to a particular embodiment, $R^{41}$, $R^{42}$, $R^{43}$ and $R^{44}$ represent a hydrogen atom.

Preferably, in these two embodiments and the alternatives thereof, $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, a halogen atom, —OR$^{55}$, —NR$^{55}$R$^{56}$, —NO$_2$ or a (C$_1$-C$_6$)alkyl group optionally substituted by a —OR$^{55}$ group, with R$^{55}$ and R$^{56}$ representing independently of each other a hydrogen atom, a CF$_3$ group or a (C$_1$-C$_6$)alkyl group, notably a hydrogen atom or a (C$_1$-C$_6$)alkyl group.

Alternatively, in these two embodiments and the alternatives thereof, $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, —OR$^{55}$, —NR$^{55}$R$^{56}$, —NO$_2$ or a (C$_1$-C$_6$)alkyl group optionally substituted by one or more substituents selected from among a halogen atom, a —OR$^{55}$, —SR$^{55}$, —NR$^{55}$R$^{56}$ and —NO$_2$ group, with R$^{55}$ and R$^{56}$ representing independently of each other a hydrogen atom or a (C$_1$-C$_6$)alkyl group.

In particular, $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, —OR$^{55}$, —NR$^{55}$R$^{56}$, —NO$_2$ or a (C$_1$-C$_6$)alkyl group optionally substituted by one or more —OR$^{55}$ groups, with R$^{55}$ and R$^{56}$ representing independently of each other a hydrogen atom or a (C$_1$-C$_6$)alkyl group.

Preferably, $R^5$ and $R^6$ represent a hydrogen atom.

Alternatively, in these two embodiments and the alternatives thereof, $R^5$ and $R^6$ form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, a halogen atom, —OR$^{55}$, —SR$^{55}$, —NR$^{55}$R$^{56}$, —NO$_2$ or a (C$_1$-C$_6$)alkyl group optionally substituted by one or more halogen atoms or —OR$^{55}$, —SR$^{55}$, —NR$^{55}$R$^{56}$ and —NO$_2$ groups, with R$^{55}$ and R$^{56}$ representing independently of each other a hydrogen atom, a (C$_1$-C$_6$)alkyl group, a —CF$_3$ group or a —COR$^{57}$ group with R$^{57}$ representing a (C$_1$-C$_6$)alkyl group or an aryl group.

Preferably, $R^{51}$, $R^{52}$, $R^{53}$ and $R^{54}$ representing independently of each other a hydrogen atom, a halogen atom, —OR$^{55}$, —NR$^{55}$R$^{56}$, —NO$_2$ or a (C$_1$-C$_6$)alkyl group optionally substituted by a —OR$^{55}$ group, with R$^{55}$ and R$^{56}$ representing independently of each other a hydrogen atom, a CF$_3$ group or a (C$_1$-C$_6$)alkyl group, notably a hydrogen atom or a (C$_1$-C$_6$)alkyl group.

Alternatively, $R^{51}$, $R^{52}$, $R^{53}$ and $R^{54}$ representing independently of each other a hydrogen atom, —OR$^{55}$, —NR$^{55}$R$^{56}$, —NO$_2$ or a (C$_1$-C$_6$)alkyl group optionally substituted by one or more substituents selected from among a halogen atom, a —OR$^{55}$, —SR$^{55}$, —NR$^{55}$R$^{56}$ and —NO$_2$ group, with R$^{55}$ and R$^{56}$ representing independently of each other a hydrogen atom or a (C$_1$-C$_6$)alkyl group.

Preferably, $R^{51}$, $R^{52}$, $R^{53}$ and $R^{54}$ representing independently of each other a hydrogen atom, —OR$^{55}$, —NR$^{55}$R$^{56}$, —NO$_2$ or a (C$_1$-C$_6$)alkyl group optionally substituted by a —OR$^{55}$ group, with R$^{55}$ and R$^{56}$ representing independently of each other a hydrogen atom or a (C$_1$-C$_6$)alkyl group.

In particular, in these two embodiments and the alternatives thereof:

$R^{41}$, $R^{42}$, $R^{43}$ and $R^{44}$ represent independently of each other a hydrogen atom, a halogen atom, —OR$^{45}$, —SR$^{45}$, —NR$^{45}$R$^{46}$ or —NO$_2$ with R$^{45}$ and R$^{46}$ representing independently of each other a hydrogen atom, a CF$_3$ group or a (C$_1$-C$_6$)alkyl group, notably a hydrogen atom or a (C$_1$-C$_6$)alkyl group, and $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, a halogen atom, —OR$^{55}$, —NR$^{55}$R$^{56}$, —NO$_2$ or a (C$_1$-C$_6$)alkyl optionally substituted by a —OR$^{55}$ group, with R$^{55}$ and R$^{56}$ representing independently of each other a hydrogen atom, a CF$_3$ group or a (C$_1$-C$_6$)alkyl group, notably a hydrogen atom or a (C$_1$-C$_6$)alkyl group.

More specifically,

R$^{41}$, R$^{42}$, R$^{43}$ and R$^{44}$ represent independently of each other a hydrogen atom, —OR$^{45}$, —NR$^{45}$R$^{46}$ or —NO$_2$ with R$^{45}$ and R$^{46}$ representing independently of each other a hydrogen atom, a CF$_3$ group or a (C$_1$-C$_6$)alkyl group, notably a hydrogen atom, or a (C$_1$-C$_6$)alkyl group, and R$^5$ and R$^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, —OR$^{55}$, —NR$^{55}$R$^{56}$, —NO$_2$ or a (C$_1$-C$_6$)alkyl group optionally substituted by one or more substituents selected from among a halogen atom, a —OR$^{55}$, —SR$^{55}$, —NR$^{55}$R$^{56}$ and —NO$_2$ group, with R$^{55}$ and R$^{56}$ representing independently of each other a hydrogen atom or a (C$_1$-C$_6$)alkyl group.

The compounds of formula (I) could notably be selected from among the following compounds:

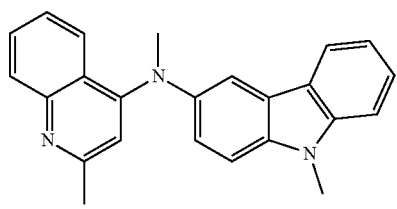

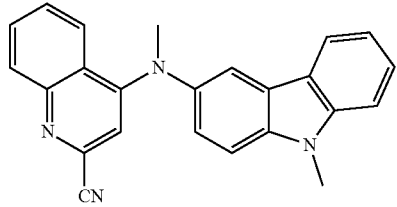

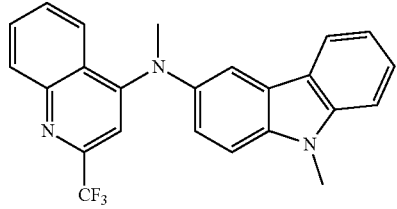

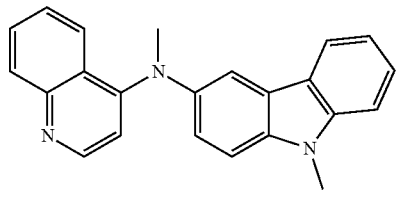

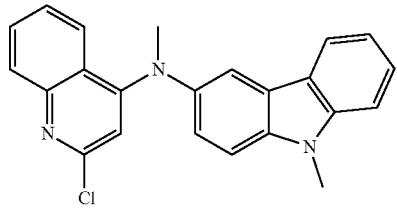

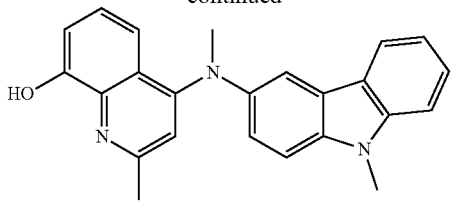

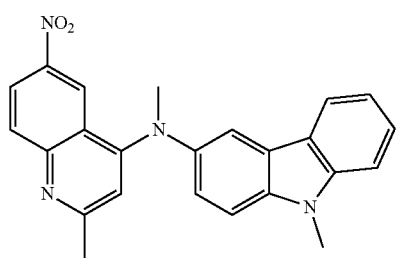

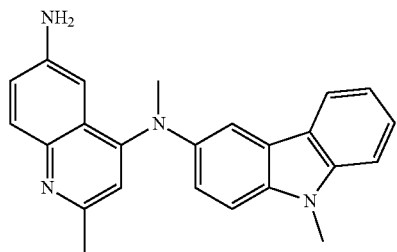

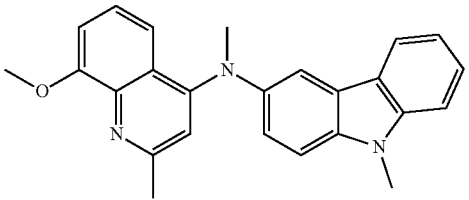

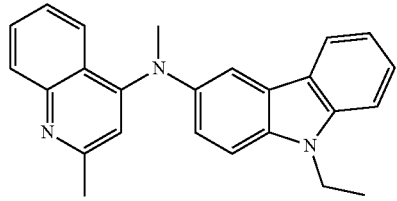

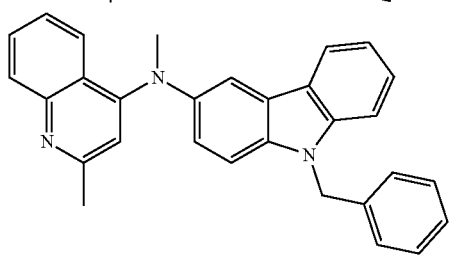

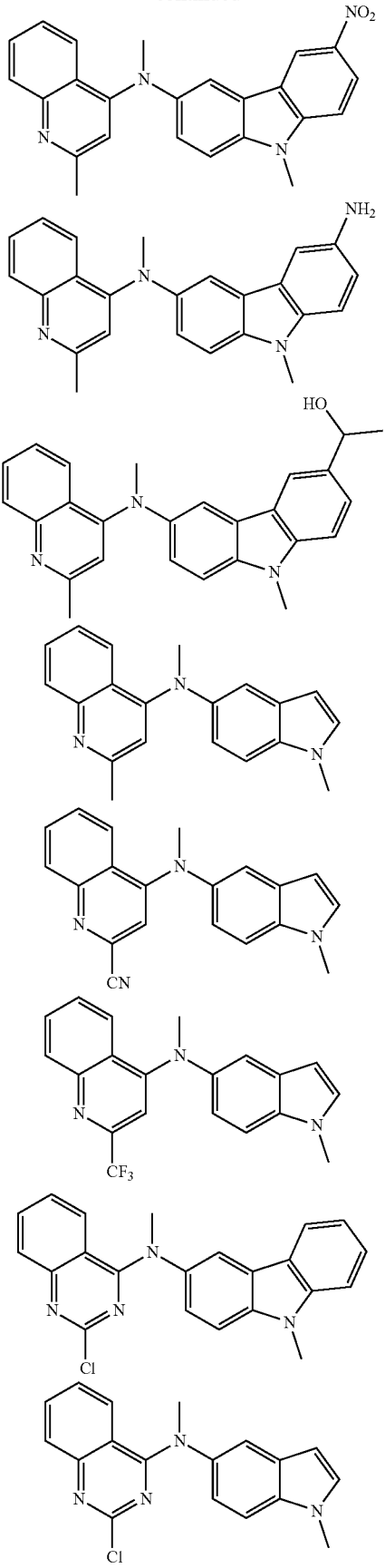

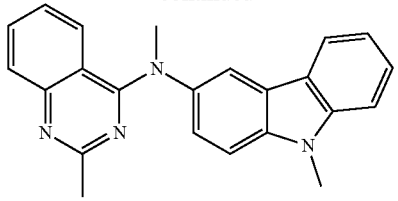

and pharmaceutically acceptable salts thereof.

Compounds of Formula (Ia) According to the Invention

According to a first particular embodiment of the invention, the compounds of formula (I) according to the invention are compounds of formula (Ia) below or a pharmaceutically acceptable salt thereof:

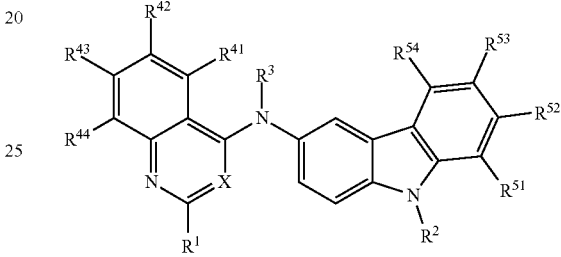

(Ia)

in which X, $R^1$, $R^2$, $R^3$, $R^{41}$, $R^{42}$, $R^{43}$, $R^{44}$, $R^{51}$, $R^{52}$, $R^{53}$ and $R^{54}$ are such as defined above.

According to a first embodiment X represents a nitrogen.

According to a second embodiment X represents a CH group.

Advantageously, in these two embodiments, according to a first alternative, $R^3$ represents a $(C_1$-$C_6)$alkyl group, preferably a methyl group.

In particular, in these two embodiments and optionally according to the first alternative, according to a second alternative $R^2$ represents a $(C_1$-$C_6)$alkyl group, preferably a methyl group, or an aryl-$(C_1$-$C_6)$alkyl group, preferably a benzyl group. More specifically, $R^2$ represents a $(C_1$-$C_6)$alkyl group, preferably a methyl group.

Preferably, in these two embodiments and the alternatives thereof, $R^{41}$, $R^{42}$, $R^{43}$ and $R^{44}$ represent independently of each other a hydrogen atom, a halogen atom, —$OR^{45}$, —$SR^{45}$, —$NR^{45}R^{46}$ or —$NO_2$ with $R^{45}$ and $R^{46}$ representing independently of each other a hydrogen atom, a $CF_3$ group or a $(C_1$-$C_6)$alkyl group, notably a hydrogen atom or a $(C_1$-$C_6)$alkyl group. In particular, $R^{41}$, $R^{42}$, $R^{43}$ and $R^{44}$ represent independently of each other a hydrogen atom, —$OR^{45}$, —$NR^{45}R^{46}$ or —$NO_2$ with $R^{45}$ and $R^{46}$ representing independently of each other a hydrogen atom, a $(C_1$-$C_6)$ alkyl group.

According to a particular embodiment, $R^{41}$, $R^{42}$, $R^{43}$ and $R^{44}$ represent a hydrogen atom.

In particular, in these two embodiments and the alternatives thereof, $R^{51}$, $R^{52}$, $R^{53}$ and $R^{54}$ representing independently of each other a hydrogen atom, a halogen atom, —$OR^{55}$, —$SR^{55}$, —$NR^{55}R^{56}$, —$NO_2$ or a $(C_1$-$C_6)$alkyl group optionally substituted by one or more halogen atoms or —$OR^{55}$, —$SR^{55}$, —$NR^{55}R^{56}$ and —$NO_2$ groups, with $R^{55}$ and $R^{56}$ representing independently of each other a hydrogen atom, a $(C_1$-$C_6)$alkyl group, a —$CF_3$ group or a —$COR^{57}$ group with $R^{57}$ representing a $(C_1$-$C_6)$alkyl group or an aryl group.

Preferably, $R^{51}$, $R^{52}$, $R^{53}$ and $R^{54}$ representing independently of each other a hydrogen atom, a halogen atom, —$OR^{55}$, —$NR^{55}R^{56}$, —$NO_2$ or a $(C_1$-$C_6)$alkyl group optionally substituted by a —$OR^{55}$ group, with $R^{55}$ and $R^{56}$ representing independently of each other a hydrogen atom, a $CF_3$ group or a $(C_1$-$C_6)$alkyl group, notably a hydrogen atom or a $(C_1$-$C_6)$alkyl group. Alternatively, $R^{51}$, $R^{52}$, $R^{53}$ and $R^{54}$ representing independently of each other a hydrogen atom, —$OR^{55}$, —$NR^{55}R^{56}$, —$NO_2$ or a $(C_1$-$C_6)$alkyl group optionally substituted by one or more substituents selected from among a halogen atom, a —$OR^{55}$, —$SR^{55}$, —$NR^{55}R^{56}$ and —$NO_2$ group, with $R^{55}$ and $R^{56}$ representing independently of each other a hydrogen atom or a $(C_1$-$C_6)$alkyl group.

Preferably, $R^{51}$, $R^{52}$, $R^{53}$ and $R^{54}$ representing independently of each other a hydrogen atom, —$OR^{55}$, —$NR^{55}R^{56}$, —$NO_2$ or a $(C_1$-$C_6)$alkyl group optionally substituted by a —$OR^{55}$ group, with $R^{55}$ and $R^{56}$ representing independently of each other a hydrogen atom or a $(C_1$-$C_6)$alkyl group.

In particular, in these two embodiments and the alternatives thereof:
- $R^{41}$, $R^{42}$, $R^{43}$ and $R^{44}$ represent independently of each other a hydrogen atom, a halogen atom, —$OR^{45}$, —$SR^{45}$, —$NR^{45}R^{46}$ or —$NO_2$ with $R^{45}$ and $R^{46}$ representing independently of each other a hydrogen atom, a $CF_3$ group or a $(C_1$-$C_6)$alkyl group, notably a hydrogen atom or a $(C_1$-$C_6)$alkyl group, and
- $R^{51}$, $R^{52}$, $R^{53}$ and $R^{54}$ representing independently of each other a hydrogen atom, a halogen atom, —$OR^{55}$, —$NR^{55}R^{56}$, —$NO_2$ or a $(C_1$-$C_6)$alkyl group optionally substituted by a —$OR^{55}$ group, with $R^{55}$ and $R^{56}$ representing independently of each other a hydrogen atom, a $CF_3$ group or a $(C_1$-$C_6)$alkyl group, notably a hydrogen atom or a $(C_1$-$C_6)$alkyl group.

More specifically,
- $R^{41}$, $R^{42}$, $R^{43}$ and $R^{44}$ represent independently of each other a hydrogen atom, —$OR^{45}$, —$NR^{45}R^{46}$ or —$NO_2$ with $R^{45}$ and $R^{46}$ representing independently of each other a hydrogen atom, a $CF_3$ group or a $(C_1$-$C_6)$alkyl group, notably a hydrogen atom, or a $(C_1$-$C_6)$alkyl group, and
- $R^{51}$, $R^{52}$, $R^{53}$ and $R^{54}$ representing independently of each other a hydrogen atom, —$OR^{55}$, —$NR^{55}R^{56}$, —$NO_2$ or a $(C_1$-$C_6)$alkyl group optionally substituted by one or more substituents selected from among a halogen atom, a —$OR^{55}$, —$SR^{55}$, —$NR^{55}R^{56}$ and —$NO_2$ group, with $R^{55}$ and $R^{56}$ representing independently of each other a hydrogen atom or a $(C_1$-$C_6)$alkyl group.

The compounds of formula (Ia) could notably be selected from among the following compounds:

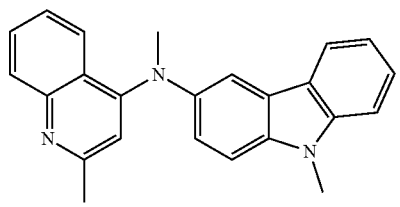 [SMILES: Cc1cc(N(C)c2ccc3c(c2)c2ccccc2n3C)c2ccccc2n1]

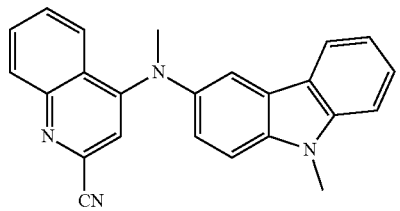 [SMILES: CN(c1ccc2c(c1)c1ccccc1n2C)c1cc(C#N)nc2ccccc12]

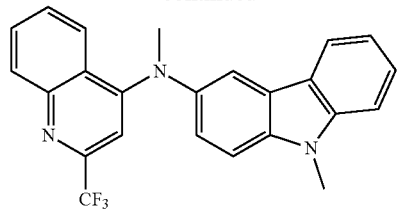 [SMILES: CN(c1ccc2c(c1)c1ccccc1n2C)c1cc(C(F)(F)F)nc2ccccc12]

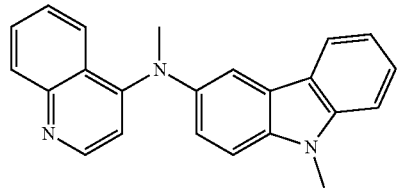

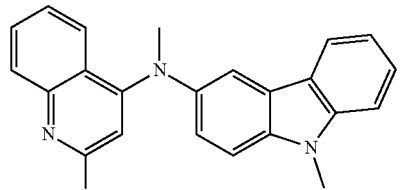

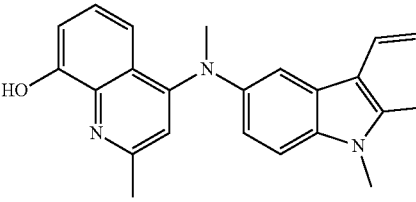

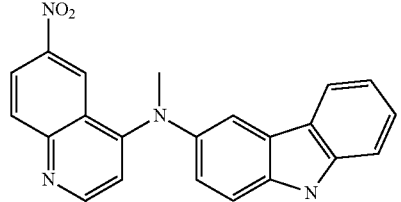

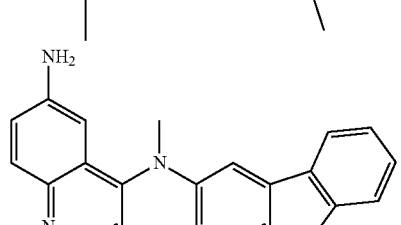

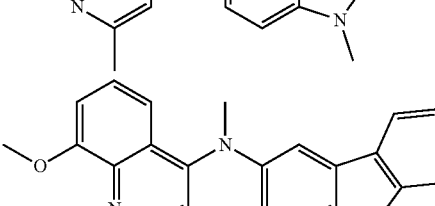

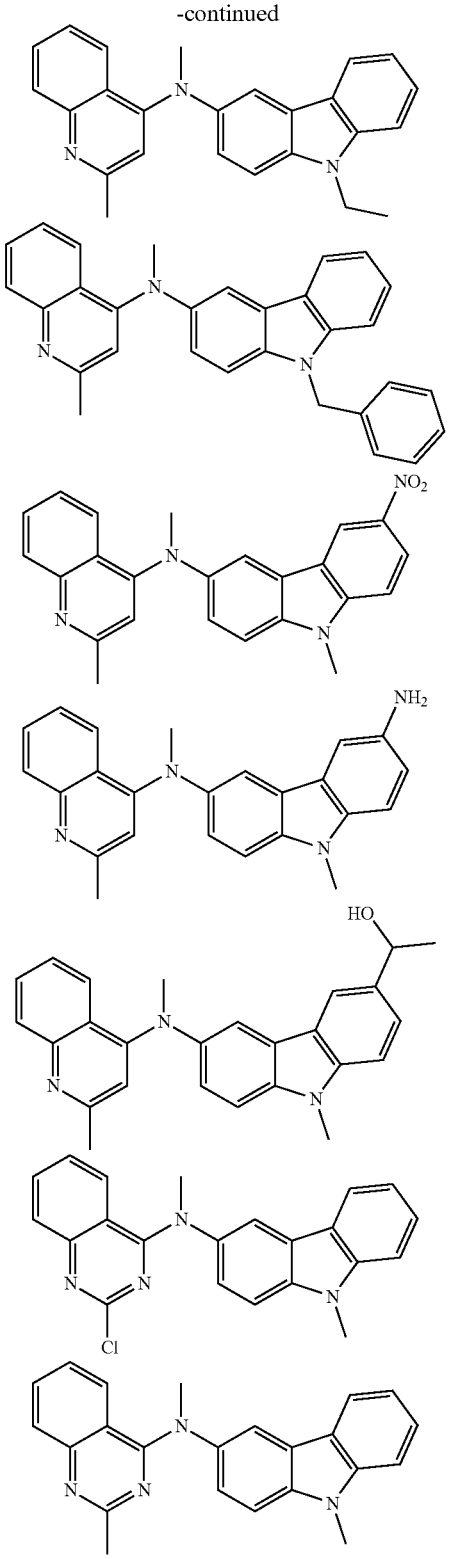

and pharmaceutically acceptable salts thereof.

Compounds Substituted by an Electron Attractor Group $R^1$ According to the Invention According to a second particular embodiment of the invention, the compounds of formula (I) according to the invention are compounds of formula (I) such as defined above in which $R^1$ represents a chlorine atom, a —CN group or a —CF$_3$ group, or a pharmaceutically acceptable salt thereof.

In particular, $R^1$ represents a chlorine atom.

According to a first embodiment X represents a nitrogen.

According to a second embodiment X represents a CH group.

Advantageously, in these two embodiments, according to a first alternative, $R^3$ represents a $(C_1-C_6)$alkyl group, preferably a methyl group.

In particular, in these two embodiments and optionally according to the first alternative, according to a second alternative, $R^2$ represents a $(C_1-C_6)$alkyl group, preferably a methyl group, or an aryl-$(C_1-C_6)$alkyl group, preferably a benzyl group. More specifically, $R^2$ represents a $(C_1-C_6)$ alkyl group, preferably a methyl group.

Preferably, in these two embodiments and the alternatives thereof, $R^{41}$, $R^{42}$, $R^{43}$ and $R^{44}$ represent independently of each other a hydrogen atom, a halogen atom, —OR$^{45}$, —SR$^{45}$, —NR$^{45}$R$^{46}$ or —NO$_2$ with R$^{45}$ and R$^{46}$ representing independently of each other a hydrogen atom, a CF$_3$ group or a $(C_1-C_6)$alkyl group, notably a hydrogen atom or a $(C_1-C_6)$alkyl group. In particular, $R^{41}$, $R^{42}$, $R^{43}$ and $R^{44}$ represent independently of each other a hydrogen atom, —OR$^{45}$, —NR$^{45}$R$^{46}$ or —NO$_2$ with R$^{45}$ and R$^{46}$ representing independently of each other a hydrogen atom, a $(C_1-C_6)$ alkyl group. More preferentially, $R^{41}$, $R^{42}$, $R^{43}$ and $R^{44}$ represent a hydrogen atom.

Preferably, in these two embodiments and the alternatives thereof, $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, a halogen atom, —OR$^{55}$, —NR$^{55}$R$^{56}$, —NO$_2$ or a $(C_1-C_6)$alkyl group optionally substituted by a —OR$^{55}$ group, with R$^{55}$ and R$^{56}$ representing independently of each other a hydrogen atom, a CF$_3$ group or a $(C_1-C_6)$ alkyl group, notably a hydrogen atom or a $(C_1-C_6)$alkyl group.

Alternatively, in these two embodiments and the alternatives thereof, $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, —OR$^{55}$, —NR$^{55}$R$^{56}$, —NO$_2$ or a $(C_1-C_6)$ alkyl group optionally substituted by one or more substituents selected from among a halogen atom, a —OR$^{55}$, —SR$^{55}$, —NR$^{55}$R$^{56}$ and —NO$_2$ group, with R$^{55}$ and R$^{56}$ representing independently of each other a hydrogen atom or a $(C_1-C_6)$alkyl group.

In particular, $R^5$ and $R^6$ represent a hydrogen atom or form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, —OR$^{55}$, —NR$^{55}$R$^{56}$, —NO$_2$ or a $(C_1-C_6)$ alkyl group optionally substituted by one or more —OR$^{55}$ groups, with R$^{55}$ and R$^{56}$ representing independently of each other a hydrogen atom or a $(C_1-C_6)$alkyl group.

Preferably, $R^5$ and $R^6$ represent a hydrogen atom.

Alternatively, in these two embodiments and the alternatives thereof, $R^5$ and $R^6$ form together a —CR$^{51}$=CR$^{52}$—CR$^{53}$=CR$^{54}$— chain with R$^{51}$, R$^{52}$, R$^{53}$ and R$^{54}$ representing independently of each other a hydrogen atom, a halogen atom, —OR$^{55}$, —SR$^{55}$, —NR$^{55}$R$^{56}$, —NO$_2$ or a $(C_1-C_6)$ alkyl group optionally substituted by one or more halogen atoms or —OR$^{55}$, —SR$^{55}$, —NR$^{55}$R$^{56}$ and —NO$_2$ groups, with R$^{55}$ and R$^{56}$ representing independently of each other a hydrogen atom, a $(C_1-C_6)$alkyl group, a —CF$_3$ group or a —COR$^{57}$ group with R$^{57}$ representing a $(C_1-C_6)$alkyl group or an aryl group.

Preferably, $R^{51}$, $R^{52}$, $R^{53}$ and $R^{54}$ representing independently of each other a hydrogen atom, a halogen atom, —$OR^{55}$, —$NR^{55}R^{56}$, —$NO_2$ or a ($C_1$-$C_6$)alkyl group optionally substituted by a —$OR^{55}$ group, with $R^{55}$ and $R^{56}$ representing independently of each other a hydrogen atom, a $CF_3$ group or a ($C_1$-$C_6$)alkyl group, notably a hydrogen atom or a ($C_1$-$C_6$)alkyl group. Alternatively, $R^{51}$, $R^{52}$, $R^{53}$ and $R^{54}$ representing independently of each other a hydrogen atom, —$OR^{55}$, —$NR^{55}R^{56}$, —$NO_2$ or a ($C_1$-$C_6$)alkyl group optionally substituted by one or more substituents selected from among a halogen atom, a —$OR^{55}$, —$SR^{55}$, —$NR^{55}R^{56}$ and —$NO_2$ group, with $R^{55}$ and $R^{56}$ representing independently of each other a hydrogen atom or a ($C_1$-$C_6$)alkyl group.

Preferably, $R^{51}$, $R^{52}$, $R^{53}$ and $R^{54}$ representing independently of each other a hydrogen atom, —$OR^{55}$, —$NR^{55}R^{56}$, —$NO_2$ or a ($C_1$-$C_6$)alkyl group optionally substituted by a —$OR^{55}$ group, with $R^{55}$ and $R^{56}$ representing independently of each other a hydrogen atom or a ($C_1$-$C_6$)alkyl group.

In particular, in these two embodiments and the alternatives thereof:

- $R^{41}$, $R^{42}$, $R^{43}$ and $R^{44}$ represent independently of each other a hydrogen atom, a halogen atom, —$OR^{45}$, —$SR^{45}$, —$NR^{45}R^{46}$ or —$NO_2$ with $R^{45}$ and $R^{46}$ representing independently of each other a hydrogen atom, a $CF_3$ group or a ($C_1$-$C_6$)alkyl group, notably a hydrogen atom or a ($C_1$-$C_6$)alkyl group, and
- $R^5$ and $R^6$ represent a hydrogen atom or form together a —$CR^{51}$=$CR^{52}$—$CR^{53}$=$CR^{54}$— chain with $R^{51}$, $R^{52}$, $R^{53}$ and $R^{54}$ representing independently of each other a hydrogen atom, a halogen atom, —$OR^{55}$, —$NR^{55}R^{56}$, —$NO_2$ or a ($C_1$-$C_6$)alkyl group optionally substituted by a —$OR^{55}$ group, with $R^{55}$ and $R^{56}$ representing independently of each other a hydrogen atom, a $CF_3$ group or a ($C_1$-$C_6$)alkyl group, notably a hydrogen atom or a ($C_1$-$C_6$)alkyl group.

More specifically,

- $R^{41}$, $R^{42}$, $R^{43}$ and $R^{44}$ represent independently of each other a hydrogen atom, —$OR^{45}$, —$NR^{45}R^{46}$ or —$NO_2$ with $R^{45}$ and $R^{46}$ representing independently of each other a hydrogen atom, a $CF_3$ group or a ($C_1$-$C_6$)alkyl group, notably a hydrogen atom, or a ($C_1$-$C_6$)alkyl group, and
- $R^5$ and $R^6$ represent a hydrogen atom or form together a —$CR^{51}$=$CR^{52}$—$CR^{53}$=$CR^{54}$— chain with $R^{51}$, $R^{52}$, $R^{53}$ and $R^{54}$ representing independently of each other a hydrogen atom, —$OR^{55}$, —$NR^{55}R^{56}$, —$NO_2$ or a ($C_1$-$C_6$)alkyl group optionally substituted by one or more substituents selected from among a halogen atom, a —$OR^{55}$, —$SR^{55}$, —$NR^{55}R^{56}$ and —$NO_2$ group, with $R^{55}$ and $R^{56}$ representing independently of each other a hydrogen atom or a ($C_1$-$C_6$)alkyl group.

The compounds substituted by an electron attracting group $R^1$ could notably be selected from among the following compounds:

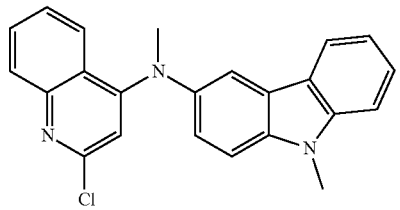

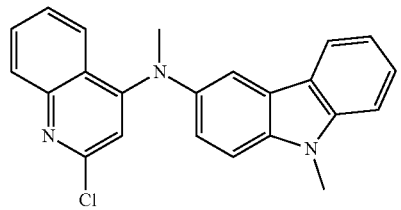

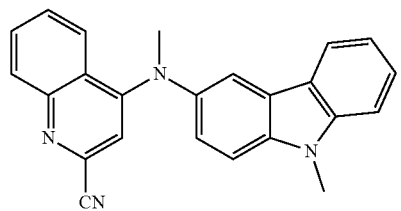

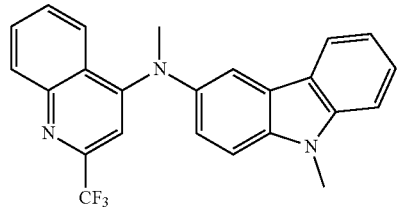

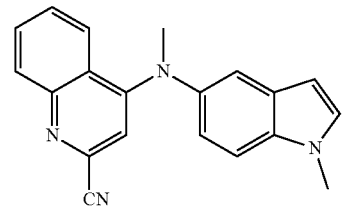

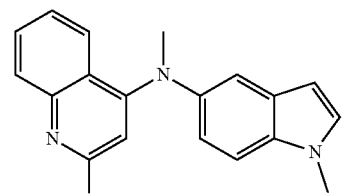

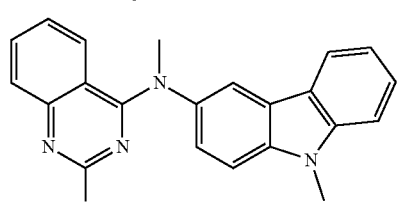

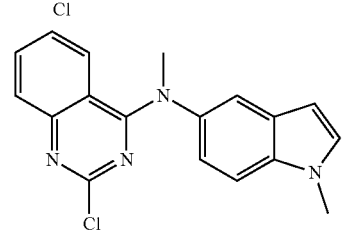

and pharmaceutically acceptable salts thereof.

In particular, the compounds substituted by an electron attracting group $R^1$ could be selected from among the following compounds:

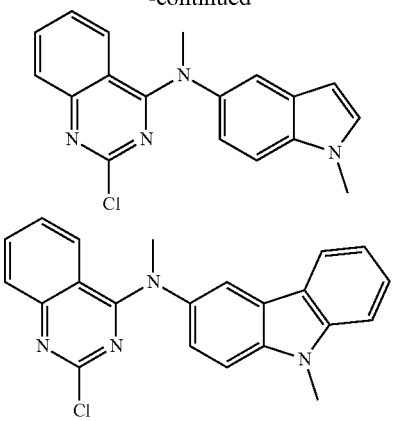

and pharmaceutically acceptable salts thereof.

Compounds of Formula (Ib) According to the Invention

According to a third particular embodiment of the invention, the compounds of formula (I) according to the invention are a compound of formula (Ib)

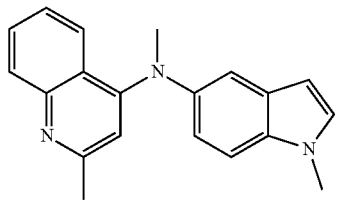
(Ib)

or a pharmaceutically acceptable salt thereof.

Uses of the Compounds According to the Invention

The invention relates to compounds of formula (I), (Ia) or (Ib) as well as pharmaceutically acceptable salts thereof, for the use thereof as a drug.

In particular, the compounds of the present invention may be used as drugs intended to treat cancer.

The present invention also relates to the use of a compound of the present invention for the preparation of a drug intended for the treatment of cancer.

The present invention also relates to a method for treating cancer comprising the administration to a patient in need thereof of an effective quantity of a compound of the present invention.

The compounds may be used alone or in association, advantageously synergic, with at least one other active principle.

Along cancers may be cited in a non-limiting manner leukaemias, lymphomas, sarcomas, melanoma, liver cancer, pancreatic cancer, lung cancer, stomach cancer, oesophageal cancer, renal cancer, cancer of the pleura, cancer of the thyroid, skin cancer, cervical cancer, breast cancer, cancer of the ovaries, colorectal cancer, testicular cancer, prostate cancer, brain cancer, cancer of the rectum, or bone cancer.

In particular, the cancer will be selected from among sarcomas, melanoma, colorectal cancer, breast cancer, cancer of the ovaries, pancreatic cancer, and leukaemias.

In particular, the patient in need of treatment is a mammal, notably a human.

Advantageously, the compounds according to the invention may be used in the treatment of cancer by acting through tubulin polymerisation inhibition and/or through immunomodulation.

Indeed, the compounds according to the invention may have at one and the same time antiproliferative activity, antivascular activity, tubulin polymerisation inhibitory activity and immunomodulatory activity.

The immunomodulatory activity of the compounds according to the invention consists in activating the immune system.

The antiproliferative activity is observed at concentrations varying from the picomolar to the nanomolar.

The immunomodulatory activity is observed through the increase in antigen presentation via a CD8+ T lymphocyte proliferation in cancerous cells in the presence of the compounds according to the invention.

The present invention also relates to a method for inhibiting tubulin polymerisation and/or activating immunomodulation comprising the administration to a patient in need thereof of an effective quantity of a compound of the present invention, alone or in association, advantageously synergic, with at least one other active principle, notably such as defined above.

Pharmaceutical Compositions According to the Invention

The invention also relates to a pharmaceutical composition comprising a compound of formula (I), (Ia), or (Ib) according to the invention, according to any one of the embodiments described above, and at least one pharmaceutically acceptable excipient.

The invention also relates to the pharmaceutical compositions according to the invention for use thereof as a drug, notably intended to treat cancer, while acting in particular through tubulin polymerisation inhibition and/or through immunomodulation.

The pharmaceutical compositions according to the invention may be intended for administration by enteral route (for example oral) or parenteral route (for example intravenous), preferably by oral or by intravenous route. The active ingredient may be administered in unitary forms for administration, mixed with conventional pharmaceutical supports, to animals, preferably mammals, in particular humans.

For oral administration, the pharmaceutical composition may be in solid or in liquid (solution or suspension) form.

A solid composition may be in the form of tablets, capsules, powders, granules and analogues. In tablets, the active ingredient may be mixed with one or more pharmaceutical vehicle(s) such as gelatine, starch, lactose, magnesium stearate, talc, gum Arabic and similar, before being compressed. The tablets may further be coated, notably with saccharose or with other suitable materials, or they may be treated in such a way that they have a prolonged or delayed activity. In powders or granules, the active ingredient may be mixed or granulated with dispersing agents, wetting agents or suspending agents and with taste correctors or sweeteners. In capsules, the active ingredient may be introduced into soft or hard capsules in the form of a powder or granule as mentioned previously or in the form of a liquid composition as mentioned hereafter.

A liquid composition may contain the active ingredient with a sweetener, a flavour enhancer or an appropriate colorant in a solvent such as water. The liquid composition may also be obtained by suspending or by dissolving a powder or granules, as mentioned above, in a liquid such as water, juice, milk, etc. It may be for example a syrup or an elixir.

For parenteral administration, the composition may be in the form of an aqueous suspension or a solution which may contain suspension agents and/or wetting agents. The composition is advantageously sterile. It may be in the form of an isotonic solution (in particular with respect to the blood).

The compounds according to the invention may be used in a pharmaceutical composition at a dose ranging from 0.01 mg to 1000 mg per day, administered in a single dose once a day or in several doses during the day, for example twice a day at equal doses. The daily administered dose is advantageously comprised between 5 mg and 500 mg, and more advantageously between 10 mg and 200 mg. However, it may be necessary to use doses outside of these ranges, which those skilled in the art will be able to take into account.

According to a particular embodiment of the invention, the compounds for the use thereof according to the invention are administered in association with another active principle, notably an anticancer compound, cytotoxic or not. Thus, the pharmaceutical composition according to the present invention may further comprise another active principle.

Thus, the pharmaceutical composition according to the invention comprises at least one compound of the present invention and at least one other active principle as combination product for simultaneous, separate or spread over time use, which may notably be used for the treatment of cancer.

Synthesis Method According to the Invention

The invention also relates to a method for preparing a compound of formula (I), (Ia) or (Ib) or a pharmaceutically acceptable salt thereof according to the invention comprising the following steps:

(1) coupling an amine derivative of following formula (II):

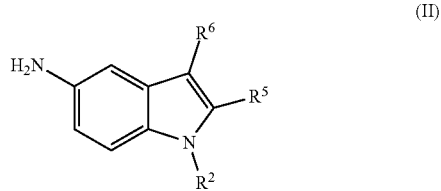

(II)

in which $R^2$, $R^5$ and $R^6$ are such as defined above, with a compound of following formula (III):

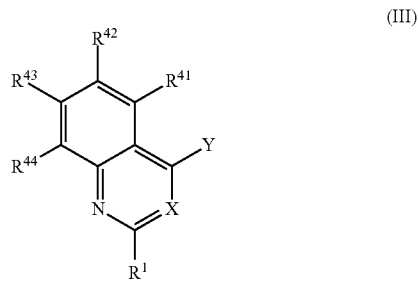

(III)

in which Y represents an atom of chlorine, bromine, iodine, a trifluoromethylsulphonate group or a tosyl group and X, $R^1$, $R^{41}$, $R^{42}$, $R^{43}$ and $R^{44}$ are such as defined above, to give a compound of formula (I), (Ia) or (Ib) such as defined above with $R^3$=H, (2) optionally substituting the $R^3$=H group borne by the amine of the compound of formula (I), (Ia) or (Ib) obtained at step (1) which precedes to give a compound of formula (I), (Ia) or (Ib) such as defined above with $R^3$ representing a ($C_1$-$C_6$)alkyl group, an aryl-($C_1$-$C_6$) alkyl group or a —$COR^{31}$ group with $R^{31}$ such as defined above, and (3) optionally salifying the compound of formula (I) obtained at step (1) or (2) which precedes to give a pharmaceutically acceptable salt of a compound of formula (I) such as defined above.

The coupling of the amine derivative of formula (II) with the compound of formula (III) may be carried out by nucleophilic aromatic substitution, preferably in acid medium, notably in the presence of hydrochloric acid.

Preferably, the coupling is carried out in an aprotic polar solvent, more preferentially, dioxane.

Advantageously, the coupling is carried out at a temperature comprised between 100 and 110° C., notably at reflux of the solvent.

The coupling of the amine derivative of formula (II) with the compound of formula (III) may also be carried out by pallado-catalysed coupling in the presence of a palladium (0) complex or a palladium (II) complex and a phosphine and in the presence of a base.

Step 2 of substitution may be a step of alkylation when $R^3$ represents a ($C_1$-$C_6$)alkyl group. The alkylation of an amine is a reaction well known to those skilled in the art who know the reaction conditions to implement.

It may be carried out for example by reaction of the amine with a ($C_1$-$C_6$)alkyl halide in the presence of a base, in particular a carbonate. Preferably, the ($C_1$-$C_6$)alkyl halide is a ($C_1$-$C_6$)alkyl iodide, a ($C_1$-$C_6$)alkyl bromide or a ($C_1$-$C_6$) alkyl chloride. In particular, the alkylation is carried out in an aprotic polar solvent, more preferentially, dimethylformamide. Preferably, the alkylation takes place at room temperature.

Step 2 of substitution may be a step of aryl-alkylation when $R^3$ represents an aryl-($C_1$-$C_6$)alkyl group. Aryl-alkylation of an amine is a reaction well known to those skilled in the art who know the reaction conditions to implement. It may be carried out in the same conditions as for the alkylation reaction described previously with an aryl-($C_1$-$C_6$)alkyl halide instead of the ($C_1$-$C_6$)alkyl halide.

Step 2 of substitution may be a step of peptide coupling when $R^3$ represents a —$COR^{31}$ group. The peptide coupling of an amine is a reaction well known to those skilled in the art who know the reaction conditions to implement. The peptide coupling may be carried out with an acyl halide (Hal-$COR^{31}$ with Hal=halogen), such as an acyl chloride (Cl$COR^{31}$), in the presence of a base, in particular triethylamine. The peptide coupling may be carried out with a carboxylic acid ($R^{31}$COOH). In this case, it will be carried out preferably in the presence of a coupling agent, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(1H-benzotriazole-1-yl)-1,1,3,3-tetramethyluronium hexafluorophosphate (HBTU), 2-(IH-benzotriazole-1-yl)-1,1,3,3-tetramethyluronium tetrafluoroborate (TBTU), O-(7-azobenzotriazol-1-yl)-1,1,3,3-tetramethyluronium hexafluorophosphate (HATU), (benzotriazol-1-yloxy)tripyrrolodinophosphonium hexafluorophosphate (PyBOP) or propylphosphonic anhydride, optionally associated with a coupling auxiliary such as N-hydroxy succinimide (NHS), N-hydroxy benzotriazole (HOBt), 3,4-dihydro-3-hydroxy-4-oxo-1,2,3-benzotriazole (HOBt), 1-hydroxy-7-azabenzotriazole (HOAt), N-hydroxysylphosuccinimide (sulpho NHS), dimethylaminopyridine (DMAP), diisopropylethylamine (DIEA) or N-methylmorpholine (NMM). Preferably, it takes place in the presence of dimethylaminopyridine.

The method for preparing a compound of formula (I), (Ia) or (Ib) according to the invention may optionally comprise a step of salification of the compound of formula (I), (Ia) or (Ib) obtained at step (1) or (2) to give a pharmaceutically acceptable salt of a compound of formula (I), (Ia) or (Ib). This involves the reaction of the compound of formula (I), (Ia) or (Ib) with a pharmaceutically acceptable acid or base.

EXAMPLES

1. Synthesis—Experimental Procedure and Product Characterisation

Into a sealed tube are added successively the chlorinated heterocyclic compound and the aromatic amine derivative in dioxane (2 mL). A drop of HCl is next added to the mixture and the reaction medium is heated to 100° C., under stirring, for 12 h. The mixture is cooled, then neutralised with NaOH$_{aq}$. (5N) and the mixture is extracted with ethyl acetate (3×10 mL). The combined organic phases are dried over Na$_2$SO$_4$ and concentrated under vacuum. The crude reaction mixture is dissolved in a solution of DMF (5 mL) containing Cs$_2$CO$_3$ (1.2 equiv.) at 0° C. To this mixture is added drop by drop CH$_3$I (1.2 equiv.) and the reaction medium is placed at room temperature, under stirring, for 12 h. The crude reaction mixture is concentrated and purified by chromatography on silica column.

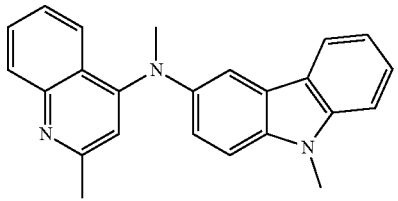

N,9-Dimethyl-N-(2-methylquinolin-4-yl)-9H-carbazol-3-amine 1 (24%). Yellow solid, MP 197.9-198.2° C. $^1$H NMR (300 MHz, CDCl$_3$) δ 8.00 (d, J=3.2 Hz, 1H), 7.97 (d, J=3.8 Hz, 1H), 7.80 (d, J=2.1 Hz, 1H), 7.61 (d, J=8.5 Hz, 1H), 7.49 (t, J=7.3 Hz, 2H), 7.39 (d, J=8.2 Hz, 1H), 7.33-7.25 (m, 1H), 7.22 (d, J=7.1 Hz, 1H), 7.17 (dd, J=8.7 Hz, J=2.1 Hz, 1H), 7.05 (t, J=7.3 Hz, 1H), 6.97 (s, 1H), 3.82 (s, 3H), 3.57 (s, 3H), 2.77 (s, 3H). $^{13}$C NMR (75 MHz, CDCl$_3$) δ 159.4, 154.4, 149.8, 143.5, 141.7, 138.0, 129.0, 128.7, 126.1, 125.3, 124.1, 123.6, 122.5, 122.2, 121.8, 120.6, 118.9, 114.8, 110.9, 109.3, 108.7, 44.2, 29.3, 25.8. IR film v$_{max}$/cm$^{-1}$: 1586, 1509, 1485, 1470, 1413, 1387, 1357, 1333, 1289, 1243, 1179, 1153, 1122, 1102, 1060.

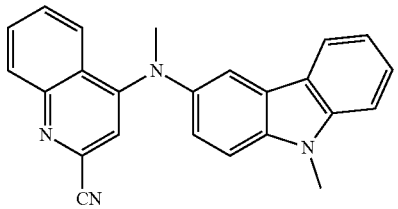

4-(Methyl(9-methyl-9H-carbazol-3-yl)amino)quinoline-2-carbonitrile 2 (28%). Pale yellow solid. MP 232.9-233.8° C. $^1$H NMR (300 MHz, CDCl$_3$) δ 7.92 (t, J=8.2 Hz, 2H), 7.75 (d, J=2.2 Hz, 1H), 7.51-7.38 (m, 3H), 7.34 (d, J=8.2 Hz, 1H), 7.26 (d, J=8.2 Hz, 1H), 7.22-7.07 (m, 3H), 7.06-6.97 (td, J=8.2 Hz, J=2.2 Hz, 1H), 3.79 (s, 3H), 3.52 (s, 3H). $^{13}$C NMR (75 MHz, CDCl$_3$) δ 154.7, 149.9, 142.2, 141.7, 138.7, 134.2, 130.3, 129.8, 126.6, 126.4, 125.7, 123.7, 122.9, 122.7, 122.2, 120.5, 119.2, 118.3, 116.3, 110.6, 109.7, 108.8, 44.8, 29.3. IR neat v$_{max}$/cm$^{-1}$: 2962, 2928, 2885, 2361, 2341, 1711, 1648, 1601, 1542, 1484, 1390, 1288, 1220, 1155, 1060, 972.

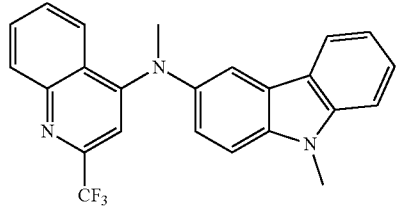

N,9-Dimethyl-N-(2-(trifluoromethyl)quinolin-4-yl)-9H-carbazol-3-amine 3 (26%). Pale yellow solid. MP 190.3-192.0° C. $^1$H NMR (300 MHz, CDCl$_3$) δ 8.06 (dd, J=7.8 Hz, J=2.2 Hz, 1H), 7.94 (d, J=7.8 Hz, 1H), 7.79 (d, J=2.2 Hz, 1H), 7.58-7.41 (m, 3H), 7.36 (d, J=8.2 Hz, 1H), 7.33-7.23 (m, 2H), 7.24-7.10 (m, 2H), 7.04 (td, J=7.8 Hz, J=6.8 Hz, 1H), 3.81 (s, 3H), 3.59 (s, 3H). $^{13}$C NMR (75 MHz, CDCl$_3$) δ 155.5, 149.1, 148.1 (q, J=135 Hz), 142.7 (2), 141.6, 138.5, 130.4, 129.5, 126.3, 126.0, 125.6, 123.7, 122.8, 122.3, 122.0 (q, J=1.1 kHz), 120.5, 119.1, 116.1, 109.6, 108.8, 104.0, 44.7, 29.2. $^{19}$F NMR (188 MHz, CDCl$_3$) δ −68.11. IR neat v$_{max}$/cm$^{-1}$: 3052, 2961, 2918, 2851, 1585, 1570, 1494, 1426, 1400, 1171, 1142, 1124, 1104, 938, 733.

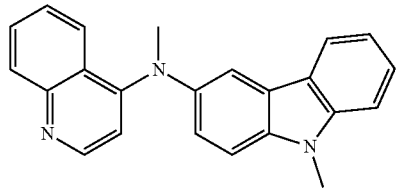 [SMILES: CN(c1ccc2c(c1)c1ccccc1n2C)c1ccnc2ccccc12]

N,9-Dimethyl-N-(quinolin-4-yl)-9H-carbazol-3-amine 4 (25%). Brown solid. MP 222.2-228.4° C. $^1$H NMR (300 MHz, DMSO) δ 8.84 (d, J=8.5 Hz, 1H), 8.54 (d, J=7.3 Hz, 1H), 8.32-8.26 (d, J=2.8 Hz, 1H), 8.26-8.13 (m, 3H), 7.91 (t, J=8.2 Hz, 1H), 7.82 (d, J=8.5 Hz, 1H), 7.67 (d, J=8.2 Hz, 1H), 7.54 (td, J=5.7 Hz, J=2.8 Hz, 2H), 7.25 (t, J=7.3 Hz, 1H), 6.71 (d, J=7.3 Hz, 1H), 4.17 (s, 3H), 3.96 (s, 3H). $^{13}$C NMR (75 MHz, DMSO) δ 155.5, 147.6, 141.3, 139.7, 138.8, 134.3, 128.1, 127.2, 126.5, 123.9, 123.8, 122.8, 121.6, 120.7, 119.2, 118.8, 118.0, 117.7, 110.5, 109.6, 99.7, 42.2, 29.3. IR neat v$_{max}$/cm$^{-1}$: 3439, 3052, 2962, 2850, 1615, 1555, 1363, 1144, 1121, 1104, 1058, 746.

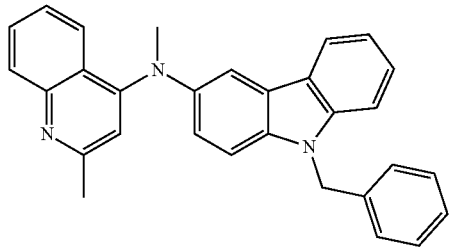 [SMILES: Cc1cc(N(C)c2ccc3c(c2)c2ccccc2n3Cc2ccccc2)c2ccccc2n1]

9-Benzyl-N-methyl-N-(2-methylquinolin-4-yl)-9H-carbazol-3-amine 5 (59%). White solid. MP 192.7-196.5° C. $^1$H NMR (300 MHz, CDCl$_3$) δ 8.67 (d, J=8.7 Hz, 1H), 8.06 (d, J=7.7 Hz, 1H), 7.96 (s, 1H), 7.58-7.41 (m, 5H), 7.30 (s, 2H), 7.26-7.14 (m, 5H), 7.02-6.94 (t, J=8.4 Hz, 1H), 6.80 (s, 1H), 5.57 (s, 2H), 3.80 (s, 3H), 3.03 (s, 3H). $^{13}$C NMR (75 MHz, CDCl$_3$) δ 157.0, 155.3 (2), 141.6, 140.8, 139.1, 136.7, 131.6, 129.0 (2), 127.9, 127.1, 126.5 (2), 126.1, 125.4, 124.4, 123.1, 123.0, 122.5, 120.9, 120.0, 119.1, 116.9, 110.7, 109.6, 106.9, 47.0, 45.7, 21.8. IR neat ν$_{max}$/cm$^{-1}$: 3062, 2823, 2360, 2201, 1630, 1595, 1507, 1482, 1380, 906.

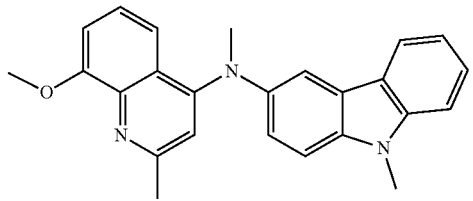 [SMILES: COc1cccc2c(N(C)c3ccc4c(c3)c3ccccc3n4C)cc(C)nc12]

N-(8-Methoxy-2-methylquinolin-4-yl)-N,9-dimethyl-9H-carbazol-3-amine 6 (45%). Yellow solid. MP 137.6-143.3° C. $^1$H NMR (300 MHz, CDCl$_3$) 8.02 (d, J=7.9 Hz, 1H), 7.86 (d, J=2.0 Hz, 1H), 7.56-7.51 (m, 1H), 7.46 (d, J=4.0 Hz, 1H), 7.41 (d, J=4.0 Hz, 1H), 7.30-7.22 (m, 2H), 6.98-6.86 (m, 4H), 4.09 (s, 3H), 3.90 (s, 3H), 3.77 (s, 3H), 3.15 (s, 3H). $^{13}$C NMR (75 MHz, CDCl$_3$) δ 156.3, 156.0, 152.4, 141.8, 141.5, 138.9, 136.5, 126.6, 124.8, 123.8, 122.6, 122.3, 121.0, 120.7, 119.4, 117.5, 117.2, 116.0, 109.8, 109.3, 108.9, 108.9, 56.2, 45.4, 29.4, 24.2. IR neat ν$_{max}$/cm$^{-1}$: 2962, 2926, 2853, 1630, 1597, 1558, 1503,

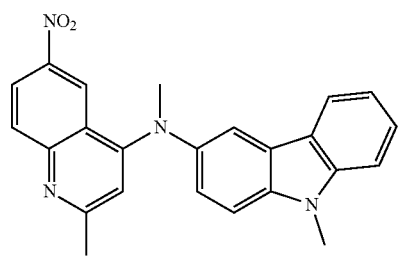 [SMILES: Cc1cc(N(C)c2ccc3c(c2)c2ccccc2n3C)c2cc([N+](=O)[O-])ccc2n1]

N,9-Dimethyl-N-(2-methyl-6-nitroquinolin-4-yl)-9H-carbazol-3-amine 7 (28%). Brown solid. MP 207.6-212.4° C. $^1$H NMR (300 MHz, CDCl$_3$) δ 8.52 (d, J=2.4 Hz, 1H), 8.16 (dd, J=7.4 Hz, J=2.4 Hz, 1H), 7.93 (d, J=6.7 Hz, 1H), 7.91 (d, J=5.1 Hz, 1H), 7.71 (s, 1H), 7.51-7.32 (m, 4H), 7.17 (t, J=7.4 Hz, 1H), 6.95 (s, 1H), 3.86 (s, 3H), 3.57 (s, 3H), 2.76 (s, 3H). $^{13}$C NMR (75 MHz, CDCl$_3$) δ 163.2, 155.6, 152.4, 142.9, 142.4, 141.7, 138.8, 130.2, 126.3, 123.8, 123.1, 123.0, 122.2, 122.1, 120.5, 120.0, 119.0, 116.2, 110.0 (2), 108.8, 44.5, 29.3, 26.0. IR film ν$_{max}$/cm$^{-1}$: 2963, 2930, 2854, 2361, 2341, 1735, 1633, 1613, 1522, 1335, 1049.

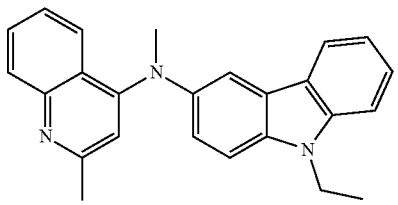 [SMILES: CCn1c2ccccc2c2cc(N(C)c3cc(C)nc4ccccc34)ccc21]

9-Ethyl-N-methyl-N-(2-methylquinolin-4-yl)-9H-carbazol-3-amine 8 (44%). Brown solid. MP 87.4-89.6° C. $^1$H NMR (300 MHz, CDCl$_3$) δ 8.55 (d, J=8.7 Hz, 1H), 8.01 (d, J=7.8 Hz, 1H), 7.91 (d, J=2.2 Hz, 1H), 7.53-7.43 (m, 4H), 7.28-7.19 (m, 3H), 6.95 (t, J=6.7 Hz, 1H), 6.86 (s, 1H), 4.40 (q, J=7.1 Hz, 2H), 3.78 (s, 3H), 2.99 (s, 3H), 1.46 (t, J=7.1 Hz, 3H). $^{13}$C NMR (75 MHz, CDCl$_3$) δ 157.1, 154.2, 140.8, 140.7, 139.7, 138.5, 131.7, 126.7, 126.3, 125.3, 124.0, 123.0, 122.2, 121.3, 120.7, 119.4, 118.4, 117.2, 110.2, 109.0, 106.0, 46.3, 37.9, 20.9, 13.9. IR film ν$_{max}$/cm$^{-1}$: 2957, 2924, 2855, 2360, 2340, 1730, 1633, 1594, 1508, 1346, 1042.

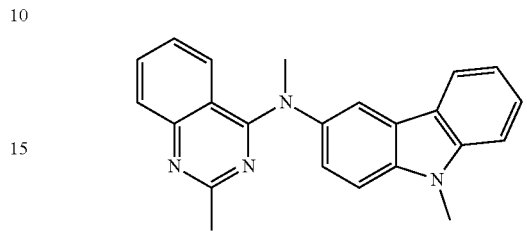

N,9-Dimethyl-N-(2-methylquinazolin-4-yl)-9H-carbazol-3-amine 9 (40%). Yellow solid. MP 181.5-183.6° C. $^1$H NMR (300 MHz, CDCl$_3$) δ 7.89 (d, J=7.7 Hz, 1H), 7.84 (d, J=2.1 Hz, 1H), 7.61 (d, J=8.4 Hz, 1H), 7.39 (q, J=6.8 Hz, 1H), 7.33 (s, 1H), 7.30 (d, J=4.2 Hz, 1H), 7.21-7.08 (m, 3H), 6.81 (d, J=8.4 Hz, 1H), 6.66 (t, J=7.7 Hz, 1H), 3.77 (s, 3H), 3.61 (s, 3H), 2.64 (s, 3H). $^{13}$C NMR (75 MHz, CDCl$_3$) δ 163.3, 161.8, 141.7, 140.4 (2), 139.4, 134.0, 131.5, 127.5, 126.4 (2), 124.3, 123.8, 122.4, 120.6, 119.3, 118.1, 114.8, 109.7, 108.8, 43.4, 29.3, 26.5. IR neat ν$_{max}$/cm$^{-1}$: 3319, 2965, 2924, 2877, 1613, 1602, 1494, 1486, 1393, 1354, 1247.

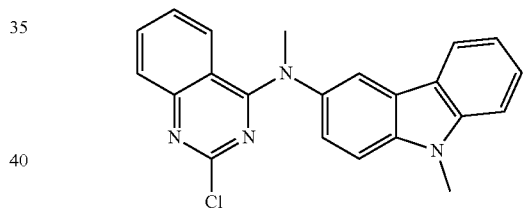

N-(2-Chloroquinazolin-4-yl)-N,9-dimethyl-9H-carbazol-3-amine 10 (62%). Pale yellow solid. MP 231.2-232.1° C. $^1$H NMR (300 MHz, CDCl$_3$) δ 8.03 (d, J=9.0 Hz, 1H), 7.98 (d, J=2.1 Hz, 1H), 7.71 (d, J=9.0 Hz, 1H), 7.60-7.40 (m, 4H), 7.34-7.27 (m, 2H), 6.80 (d, J=4.1 Hz, 2H), 3.91 (s, 3H), 3.74 (s, 3H). $^{13}$C NMR (75 MHz, CDCl$_3$) δ 162.9, 156.8, 153.2, 141.9, 139.9, 138.9, 132.6, 127.7, 126.8, 126.7, 125.0, 124.3, 124.1, 122.4, 120.8, 119.6, 118.4, 115.1, 110.1, 109.1, 44.1, 29.5. IR neat ν$_{max}$/cm$^{-1}$: 3053, 2930, 1632, 1600, 1528, 1504, 1469, 1393, 927.

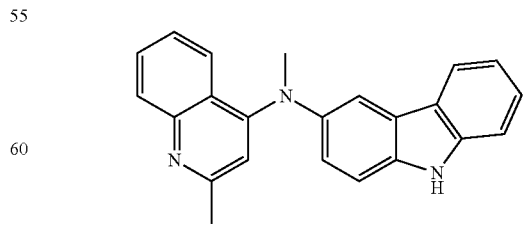

N-Methyl-N-(2-methylquinolin-4-yl)-9H-carbazol-3-amine 11 (12%). Into a dry sealed tube purged with argon is added 5 (85 mg, 0.2 mmol) in trifluoroacetic acid (3 mL)

with 4 drops of triflic acid. The mixture is heated to 85° C., under stirring, for 4 h. The reaction medium is cooled and dichloromethane (20 mL) is added. The organic phase is washed with water (20 mL), dried over Na$_2$SO$_4$ and filtered on filter paper. The filtrate is concentrated and purified by chromatography on silica column with a dichloromethane/methanol mixture [95;5] and 11 is obtained (8 mg, 12%). Yellow solid. MP 147.5-149.2° C. $^1$H NMR (400 MHz, MeOD) δ 7.96-7.93 (m, 2H), 7.77 (d, J=8.3 Hz, 1H), 7.57 (t, J=7.4 Hz, 1H), 7.53 (d, J=8.6 Hz, 1H), 7.46 (d, J=8.1 Hz, 1H), 7.38 (t, J=7.4 Hz, 1H), 7.28-7.20 (m, 2H), 7.12 (t, J=7.4 Hz, 1H), 7.04 (s, 1H), 6.95 (t, J=7.4 Hz, 1H), 3.73 (s, 3H), 2.76 (s, 3H). $^{13}$C NMR (101 MHz, MeOD) δ 158.9, 155.6, 142.4, 142.2, 141.2, 140.2, 133.1, 129.1, 128.1, 127.5, 126.0, 125.5, 124.2, 123.8, 121.7, 121.3, 120.2, 118.2, 113.5, 112.2, 106.8, 46.4, 20.9. IR neat $v_{max}$/cm$^{-1}$: 3471, 3065, 3026, 2413, 2360, 1732, 1668, 1614, 1579, 1521, 1488, 1261, 1161, 1016.

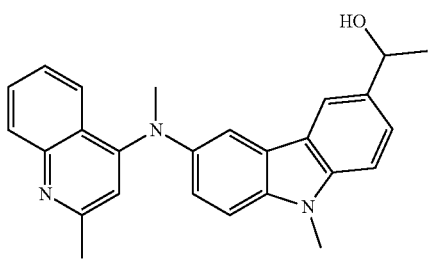 [SMILES: Cc1cc(N(C)c2ccc3c(c2)c2cc(C(C)O)ccc2n3C)c2ccccc2n1]

1-(9-Methyl-6-(methyl(2-methylquinolin-4-yl)amino)-9H-carbazol-3-yl)ethanol 12 (80%). Into a 5 mL two-neck flask is added 1 (40 mg, 0.11 mmol), AlCl$_3$ (15 mg, 0.11 mmol, 1 equiv.) and dichloromethane (3 mL). The reaction medium is heated to reflux and acetyl chloride (8 μL, 0.11 mmol, 1 equiv.) is added drop by drop. The reaction medium is heated to reflux for 4 h. The solvent is evaporated under vacuum and a dichloromethane/water mixture [1;1] (1 mL) is added. Sodium borohydride NaBH$_4$ (7 mg, 0.11 mmol, 1 equiv.) is added slowly to the reaction medium, then the whole is placed at room temperature and under stirring for 4 h. Water is added slowly and the aqueous phase is extracted with dichloromethane. The organic phases are combined together, dried over Na$_2$SO$_4$, then filtered on filter paper. The filtrate is concentrated and purified by chromatography on silica column with a dichloromethane/methanol mixture [95;5] and 12 is obtained (35 mg, 80%). Yellow solid. MP 152.4-156.8° C. $^1$H NMR (300 MHz, MeOD) δ 8.05 (s, 2H), 7.82 (d, J=8.3 Hz, 1H), 7.69-7.51 (m, 5H), 7.41 (dd, J=8.8 Hz, J=1.4 Hz, 1H), 7.34 (d, J=8.5 Hz, 1H), 7.16 (s, 1H), 7.05 (t, J=8.3 Hz, 1H), 5.02 (q, J=6.6 Hz, 1H), 3.95 (s, 3H), 3.81 (s, 3H), 2.82 (s, 3H), 1.55 (d, J=6.6 Hz, 3H). $^{13}$C NMR (75 MHz, MeOD) δ 158.5, 157.2, 146.8, 143.2, 142.5, 140.5, 138.4, 131.1, 127.3, 125.6, 125.5 125.3, 124.9, 124.0, 123.3, 121.2, 118.3, 117.2, 111.0, 109.7, 71.2, 49.0, 45.5, 29.5 (2), 25.9. IR neat $v_{max}$/cm$^{-1}$: 3407, 2924, 2853, 2341, 1635, 1596, 1509, 1490, 1424, 1348, 1179, 1072, 1007.

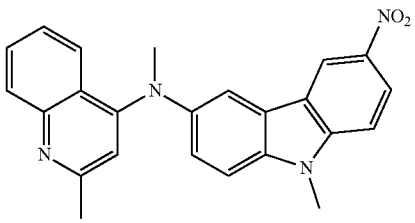

N,9-dimethyl-N-(2-methylquinolin-4-yl)-6-nitro-9H-carbazol-3-amine 13 (72%). To a solution of 1 (600 mg, 1.709 mmol) in dichloromethane (30 mL) is added drop by drop HNO$_3$ (69%, 111 μL, 1 eq.) at 0° C. under argon. After complete addition of HNO$_3$, the reaction medium is left under stirring at room temperature for 3 h. The medium is concentrated, purified by chromatography on silica column with a dichloromethane/methanol mixture [95;5], and 13 is obtained (487 mg, 72%) after recrystallisation in a cyclohexane/dichloromethane mixture [80;20]. Orange crystals. MP 182.4-183.4° C. $^1$H NMR (300 MHz, CDCl3) δ 7.92 (t, J=8.0 Hz, 2H), 7.62 (d, J=8.1 Hz, 1H), 7.58 (d, J=7.3 Hz, 1H), 7.49-7.43 (m, 2H), 7.32 (t, J=8.6 Hz, 2H), 7.03 (m, 2H), 6.93 (s, 1H), 3.85 (s, 3H), 3.46 (s, 3H), 2.74 (s, 3H). $^{13}$C NMR (75 MHz, CDCl$_3$) δ 159.1, 153.2, 149.7, 142.1, 140.9, 139.7, 134.5, 129.1, 128.9, 127.9, 124.6, 124.5, 124.3, 122.0, 121.0, 120.5, 118.6, 115.0, 111.8, 109.6, 109.3, 44.2, 29.5, 25.9. IR film $v_{max}$/cm$^{-1}$: 2957, 2832, 2341, 1845, 1734, 1684, 1559, 1525, 1475, 1157, 682.

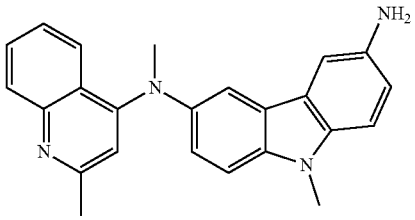 [SMILES: Cc1cc(N(C)c2ccc3c(c2)c2cc(N)ccc2n3C)c2ccccc2n1]

N3,9-dimethyl-N3-(2-methylquinolin-4-yl)-9H-carbazole-3,6-diamine 14 (87%). Into a 25 mL two-neck flask is added 13 (100 mg, 0.25 mmol) and Pd/C (10%, 6 mg, 0.02 eq.) in ethanol (3 mL). Hydrated hydrazine is added slowly to the reaction medium and the whole is heated to reflux, under stirring for 6 h. The crude reaction mixture is cooled to room temperature and filtered on Celite. The filtrate is concentrated and purified by chromatography on silica column with a dichloromethane/ethanol mixture [90;10] and 14 is obtained (143 mg, 87%). Yellow solid. MP 137.8-138.3° C. $^1$H NMR (300 MHz, MeOD) δ 8.78 (d, J=8.4 Hz, 1H), 8.04 (t, J=7.6 Hz, 1H), 7.93 (d, J=8.2 Hz, 1H), 7.85 (t, J=7.6 Hz, 1H), 7.59 (d, J=8.8 Hz, 1H), 7.55 (d, J=8.2 Hz, 1H), 7.44 (d, J=8.2 Hz, 1H), 7.35 (t, J=7.5 Hz, 1H), 7.16 (d, J=8.8 Hz, 1H), 6.85 (t, J=7.6 Hz, 1H), 6.09 (s, 1H), 3.87 (s, 3H), 2.90 (s, 3H), 2.40 (s, 3H). $^{13}$C NMR (75 MHz, MeOD) δ 157.8, 155.9, 143.0, 141.3, 140.6, 136.4, 134.8, 128.0, 127.0, 124.3, 122.5, 121.5, 121.2, 121.0, 119.4, 117.9, 115.7, 112.7, 111.2, 109.8, 101.4, 31.8, 29.4, 20.4. IR film $v_{max}$/cm$^{-1}$: 2924, 2853, 2341, 2327, 2273, 1845, 1734, 1635, 1603, 1558, 1521, 1474, 1438, 1365, 1338, 1090.

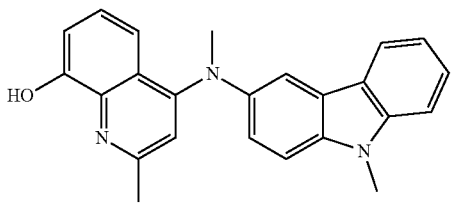 [SMILES: Cc1cc(N(C)c2ccc3c(c2)c2ccccc2n3C)c2cccc(O)c2n1]

2-Methyl-4-(methyl(9-methyl-9H-carbazol-3-yl)amino) quinolin-8-ol 15. To a solution of 6 (20 mg, 0.052 mmol) in dry dichloromethane (1 mL) is added drop by drop BBr$_3$ (10 µL, 2 eq.) at −50° C. under argon. After complete addition of BBr$_3$, the reaction medium is left under stirring at room temperature for 2 h. The pH of the reaction medium is adjusted to pH=8 by means of an aqueous solution of NaHCO$_3$, then the organic phase is isolated and the aqueous phase is extracted with dichloromethane. The organic phases are combined together and dried over Na$_2$SO$_4$, then filtered on filter paper. The filtrate is concentrated and purified by chromatography on silica column with a dichloromethane/methanol mixture [95;5] and 15 is obtained (17 mg, 87%). Brown solid. MP 222.4-223.4° C. $^1$H NMR (300 MHz, CDCl$_3$) δ 7.97 (d, J=7.8 Hz, 1H), 7.80 (d, J=2.1 Hz, 1H), 7.47 (t, J=8.7 Hz, 1H), 7.39 (d, J=8.2 Hz, 1H), 7.29 (d, J=8.7 Hz, 1H), 7.22-7.15 (m, 2H), 6.97-6.84 (m, 4H), 3.84 (s, 3H), 3.55 (s, 3H), 2.70 (s, 3H). $^{13}$C NMR (75 MHz, CDCl$_3$) δ 157.1, 154.5, 152.0, 143.2, 141.7, 139.6, 138.3, 126.2, 124.6, 123.6 (2), 122.7, 121.5, 120.6, 119.0, 115.9, 115.4, 110.7, 109.4, 108.9, 108.8, 44.4, 29.4, 25.3. IR neat $v_{max}$/cm$^{-1}$: 3051, 2878, 2360, 1564, 1511, 1484, 1471, 1424, 1357, 1293, 1243, 1083.

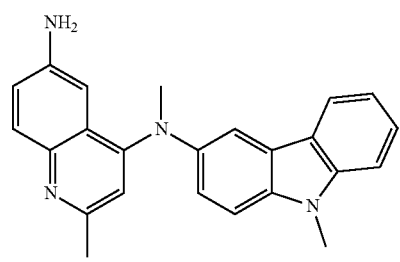 [SMILES: Cc1cc(N(C)c2ccc3c(c2)c2ccccc2n3C)c2cc(N)ccc2n1]

N4,2-Dimethyl-N4-(9-methyl-9H-carbazol-3-yl)quinoline-4,6-diamine 16. Into a 25 mL two-neck flask is added 7 (180 mg, 0.45 mmol) to an ethanol/water mixture [8;2]. The reaction medium is heated to 90° C. up to complete solubilisation of 7. Solid Fe (254 mg, 4.5 mmol, 10 equiv.) and 3 drops of HCl are added to the reaction medium and the whole is heated to 90° C., under stirring for 4 h. The crude reaction mixture is cooled to room temperature and filtered on filter paper. The filtrate is concentrated and purified by chromatography on silica column with a dichloromethane/ethanol mixture [95;5] and 16 is obtained (143 mg, 87%). Pale yellow solid. MP 192.6-196.5° C. $^1$H NMR (300 MHz, CDCl$_3$) δ 8.02 (d, J=7.7 Hz, 2H), 7.81 (d, J=2.1 Hz, 1H), 7.52 (t, J=7.5 Hz, 1H), 7.42 (d, J=8.2 Hz, 1H), 7.34 (d, J=8.5 Hz, 1H), 7.24 (t, J=7.5 Hz, 1H), 7.15 (dd, J=7.7 Hz, 2.1 Hz, 1H), 6.98 (d, J=11.1 Hz, 1H), 6.83 (s, 1H), 6.57 (s, 1H), 4.78 (s, 2H), 3.87 (s, 3H), 3.60 (s, 3H), 2.79 (s, 3H). $^{13}$C NMR (75 MHz, CDCl$_3$) δ 155.8, 153.0, 143.3, 142.9, 141.7, 137.6, 134.4, 130.2, 126.0, 123.6, 123.5, 122.6, 121.2, 120.8, 120.6, 118.8, 113.2, 112.9, 109.2, 108.7, 106.4, 43.7, 29.3, 25.3. IR neat $v_{max}$/cm$^{-1}$: 2928, 2360, 2341, 1744, 1623, 1470, 1426, 1248, 1122.

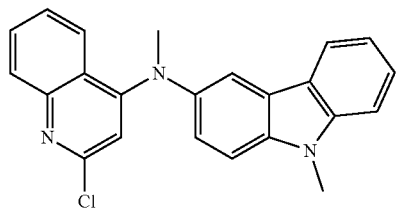 [SMILES: CN(c1ccc2c(c1)c1ccccc1n2C)c1cc(Cl)nc2ccccc12]

N-(2-Chloroquinolin-4-yl)-N,9-dimethyl-9H-carbazol-3-amine 17. Into a dry tube purged with argon are added successively 2-hydroxyquinolin-4-yl triflate (26 mg, 0.14 mmol, 1 equiv.), 9-methyl-9H-carbazol-3-amine (40 mg, 0.21 mmol, 1.5 equiv.), Pd$_2$dba$_3$ (8 mg, 6%), ±BINAP (11 mg, 12%), Cs$_2$CO$_3$ (112 mg, 2.5 equiv.) in dry dioxane (1.7 mL). The reaction medium is heated to 130° C., under microwave irradiation for 1.5 h. The reaction medium is cooled to room temperature, then filtered on Celite using a dichloromethane/methanol mixture [8; 2]. The filtrate is concentrated and POCl$_3$ (3 mL) is added slowly. NEt$_3$ (0.5 mL) is added drop by drop to the reaction medium, then the whole is heated to 90° C., under stirring for 4 h. The POCl$_3$ is distilled under vacuum and ethyl acetate (20 mL) is added. The organic phase is washed with a solution of NaHCO$_3$, dried over Na$_2$SO$_4$ and filtered on filter paper. The filtrate is concentrated and added to a solution of Cs$_2$CO$_3$ (70 mg, 1.5 equiv.) in DMF (5 mL) at 0° C. CH$_3$I (14 µL, 1.5 equiv.) is added drop by drop at 0° C. to the crude reaction mixture which is left at room temperature, under stirring for 12 h. The crude reaction mixture is concentrated and purified by chromatography on silica column with a cyclohexane/ethyl acetate mixture [90;10] and 17 is obtained (4 mg, 8%). Yellow solid. MP 137.5-139.2° C. $^1$H NMR (300 MHz, CDCl$_3$) δ 7.98 (d, J=7.8 Hz, 1H), 7.89 (dd, J=8.8 Hz, J=1.4 Hz, 1H), 7.81 (d, J=2.2 Hz, 1H), 7.51-7.43 (m, 3H), 7.40 (d, J=8.2 Hz, 1H), 7.32 (d, J=8.8 Hz, 1H), 7.24-7.16 (m, 2H), 7.02-6.96 (m, 2H), 3.85 (s, 3H), 3.55 (s, 3H). $^{13}$C NMR (75 MHz, CDCl$_3$) δ 156.1, 151.7, 149.4, 142.8, 141.8, 138.6, 129.6, 129.0, 126.4, 125.9, 124.9, 123.8, 122.9, 122.4, 121.7, 120.7, 119.2, 116.2, 109.6, 109.1, 108.9, 44.9, 29.4. IR neat $v_{max}$/cm$^{-1}$: 2937, 2351, 2312, 1795, 1656, 1445, 1427, 1289, 1101.

General procedure for synthesising the compounds 18-20. Into a dry sealed tube purged with argon are added successively the chlorinated aromatic derivative, 1-methyl-1H-indol-5-amine, Pd$_2$dba$_3$ (10 mol %), Xphos (20 mol %), NaOtBu (3 equiv.) in dry toluene (2 mL). The reaction medium is heated to 100° C., under stirring for 12 h. The reaction medium is cooled to room temperature, filtered on Celite. The filtrate is concentrated and added to a solution of Cs$_2$CO$_3$ (70 mg, 1.5 equiv.) in DMF (5 mL) at 0° C. CH$_3$I (14 µL, 1.5 equiv.) is added drop by drop at 0° C. to the crude reaction mixture and the whole is left at room temperature under stirring for 12 h. The crude reaction mixture is concentrated then is purified by chromatography on silica column.

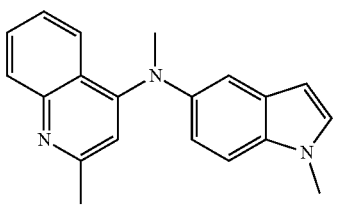 [SMILES: Cc1cc(N(C)c2ccc3c(ccn3C)c2)c2ccccc2n1]

N,2-Dimethyl-N-(1-methyl-1H-indol-5-yl)quinolin-4-amine 18 (14%). Beige solid, MP 130.5-132.2° C. $^1$H NMR (300 MHz, CDCl$_3$) δ 7.94 (d, J=8.3 Hz, 1H), 7.61 (d, J=8.4 Hz, 1H), 7.48 (t, J=7.6 Hz, 1H), 7.29 (d, J=2.0 Hz, 1H), 7.22 (d, J=8.7 Hz, 1H), 7.10-7.02 (m, 2H), 6.96 (dd, J=8.7 Hz, J=2.0 Hz, 1H), 6.91 (s, 1H), 6.38 (d, J=3.0 Hz, 1H), 3.78 (s, 3H), 3.50 (s, 3H), 2.74 (s, 3H). $^{13}$C NMR (75 MHz, CDCl$_3$) δ 159.4, 154.6, 149.7, 144.0, 134.0, 129.9, 129.2, 128.9, 128.7, 125.4, 124.0, 121.9, 118.7, 115.0, 110.8, 110.2, 101.0, 44.2, 33.1, 25.8. IR neat $v_{max}$/cm$^{-1}$: 1585, 1509, 1486, 1393, 1366, 1338, 1294, 1263, 1174, 1151, 1107, 1095, 1078, 1031.

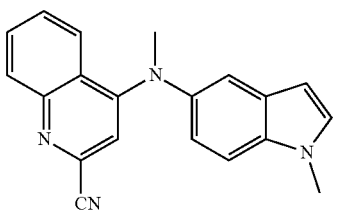 [SMILES: CN(c1ccc2c(ccn2C)c1)c1cc(C#N)nc2ccccc12]

4-(Methyl(1-methyl-1H-indol-5-yl)amino)quinoline-2-carbonitrile 19 (73%). Brown solid. MP 173.1-174.2° C. $^1$H NMR (300 MHz, CDCl$_3$) δ 7.99 (d, J=8.4 Hz, 1H), 7.58-7.48 (m, 2H), 7.32 (d, J=2.0 Hz, 1H), 7.29 (s, 1H), 7.18 (s, 1H), 7.15-7.07 (m, 2H), 6.96 (dd, J=8.4, J=2.0 Hz, 1H), 6.40 (d, J=2.0 Hz, 1H), 3.80 (s, 3H), 3.53 (s, 3H). $^{13}$C NMR (75 MHz, CDCl$_3$) δ 155.0, 150.0, 142.8, 134.7, 134.2, 130.4, 130.3, 129.9, 129.3, 126.6, 125.9, 122.9, 119.2, 118.4, 116.7, 110.7, 110.6, 101.3, 44.8, 33.2. IR neat $v_{max}$/cm$^{-1}$: 2968, 2955, 2926, 2853, 2359, 1751, 1632, 1565, 1488, 1380, 1307, 1244, 1109, 1032, 909.

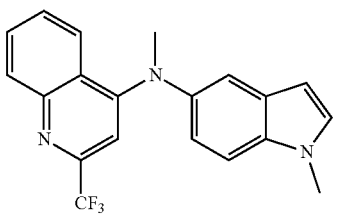 [SMILES: CN(c1ccc2c(ccn2C)c1)c1cc(C(F)(F)F)nc2ccccc12]

N-Methyl-N-(1-methyl-1H-indol-5-yl)-2-(trifluoromethyl)quinolin-4-amine 20 (62%). Pale yellow solid. MP 108.5-109.5° C. $^1$H NMR (300 MHz, CDCl$_3$) δ 8.02 (d, J=8.5 Hz, 1H), 7.54-7.43 (m, 2H), 7.27 (d, J=2.0 Hz, 1H), 7.19 (d, J=7.6 Hz, 2H), 7.09-6.99 (m, 2H), 6.91 (dd, J=8.5 Hz, J=2.0 Hz, 1H), 6.33 (d, J=3.1 Hz, 1H), 3.73 (s, 3H), 3.49 (s, 3H). $^{13}$C NMR (75 MHz, CDCl$_3$) δ 155.7, 149.0, 148.4 (q, J=33 Hz), 143.2, 134.4, 130.3, 130.1, 129.4, 129.1, 125.9, 125.7, 122.9, 122.0 (q, J=273 Hz), 119.0, 116.3, 110.5, 103.8, 101.1, 44.6, 33.0. $^{19}$F NMR (188 MHz, CDCl$_3$) δ −67.84. IR neat cm$^{-1}$: 2963, 2926, 2853, 1598, 1569, 1513, 1488, 1365, 1189, 1154, 1128, 1111, 1093.

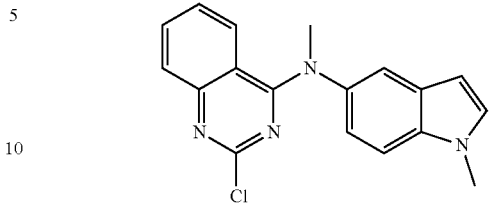

2-Chloro-N-methyl-N-(1-methyl-1H-indol-5-yl)quinazolin-4-amine 21. Into a dry sealed tube purged with argon are added successively 2,4-dichloroquinazoline (139 mg, 0.70 mmol, 1 equiv), 1-methyl-1H-indol-5-amine (83 mg, 0.84 mmol, 1.2 equiv) and t-BuOK (102 mg, 0.91 mmol, 1.3 equiv) in a THF/water mixture [2:1] (10 mL). The reaction medium is stirred at room temperature for 48 h. H$_2$O (40 mL) is added to the reaction medium and the mixture is extracted with ethyl acetate. The organic phases are combined together, dried over Na$_2$SO$_4$ and filtered on filter paper. The filtrate is concentrated under vacuum and is added to a solution of NaH (84 mg, 3.5 mmol, 5 equiv) in DMF (5 mL) at 0° C. Methyl iodide (CH$_3$I, 218 μL, 2.5 mmol, 5 equiv) is added drop by drop at 0° C. to the reaction medium which is next left at room temperature, under stirring, for 12 h. The crude reaction mixture is concentrated and purified by chromatography on silica column with a dichloromethane/methanol mixture [90:10] and the compound 21 is obtained (16 mg, 10%). White solid, MP 173.2-176.6° C. $^1$H NMR (300 MHz, CDCl$_3$) δ 8.11 (d, J=7.7 Hz, 1H), 8.05 (d, J=1.9 Hz, 1H), 8.02 (d, J=9.3 Hz, 1H), 7.88 (d, J=8.1 Hz, 1H), 7.65 (t, J=7.6 Hz, 1H), 7.57 (t, J=7.6 Hz, 1H), 7.48 (t, J=9.3 Hz, 2H), 7.41 (dd, J=8.6 Hz, J=2.0 Hz, 1H), 7.32 (m, 2H), 6.76 (s, 1H), 3.91 (s, 3H), 3.75 (s, 3H). $^{13}$C NMR (75 MHz, CDCl$_3$) δ 157.7, 148.8, 142.1, 141.7, 139.7, 137.5, 130.5, 126.9, 126.4, 125.5, 124.1, 122.8, 122.5, 121.4, 120.6, 119.5, 119.4, 111.5, 110.0, 108.9, 39.6, 29.3. IR neat $v_{max}$/cm$^{-1}$: 1565, 1503, 1488, 1445, 1423, 1399, 1365, 1334, 1301, 1281, 1268, 1243, 1208, 1168, 1093, 1013.

2. Biological Studies 2.1. In Vitro Cytotoxicity Study

The effects of the compounds according to the invention on the proliferation of different cancerous cells as well as on the proliferation of endothelial cells were studied.

The biological activity of the compounds of the invention were studied in vitro on 5 human cancer cell lines of different tissular origins: HCT116 colorectal carcinoma; A2780R Cisplatin resistant ovary cancer; MiaPaca2 pancreatic cancer; K562R Doxorubicin resistant chronic myeloid leukaemia; JIM-T1 Trastuzumab-DM1 resistant mammal carcinoma; and HepG2 hepatic carcinoma. The cells selected for this study were incubated at 37° C. in the presence of one of the compounds added to the culture medium at different concentrations. The series of experiments carried out made it possible to determine the degree of toxicity of the compound tested, its effect on cell cycle progression as well as its capacity to induce cell death by apoptosis.

All the cell lines were maintained in culture at 37° C. in a humid atmosphere containing 5% CO$_2$. Cell viability was evaluated using the reagent CellTiter-Blue™ (Promega, WI, USA) while respecting the manufacturer's instructions. The cells were seeded in 96 well culture plates at a rate of 5000 cells per 15 wells in 50 µl of culture medium. After 24 hours of culture, the compounds of generic formula (I) dissolved in DMSO were added individually to each of the wells at a rate of 50 µl per well. All the compounds were tested in triplicate for each concentration defined and each experiment was repeated 3 times. After 72 hours of incubation, 20 µL of resazurin were added to each well. After 2 hours of incubation, the fluorescence emitted was measured at 590 nm after excitation at 560 nm by means of a Victor type fluorescence reader (Perkin-Elmer, USA). The concentration of each of the compounds that induce the death of 50% of cells ($IC_{50}$) was determined after 72 hours of incubation.

The results are reported in table 1 below and in the table 2 in the following paragraph 2.2.

TABLE 1

Toxicity results of compounds 1 and 21 on six human cancer cell lines.

| Compound | $IC_{50}$ (nM) | | | | |
| --- | --- | --- | --- | --- | --- |
| | HCT116 | A2780R | MiaPaca2 | K562R | JIM-T1 |
| 1 | 0.07 ± 0.09 | 0.54 ± 0.094 | 0.47 ± 0.010 | 0.277 ± 0.017 | 0.36 ± 0.020 |
| 21 | 0.20 ± 0.01 | 2.34 ± 0.180 | 0.62 ± 0.016 | 1.77 ± 0.162 | 0.52 ± 0.016 |

2.2. Tubulin Polymerisation Inhibition

The tubulin is purified from ewe brains according to the Shelanski method by 2 assembly-disassembly cycles. The mother solution (15-20 mg/mL), stored at −196° C., is thawed and diluted in the assembly buffer (0.1 M MES, 0.5 mM $MgCl_2$, 1 mM EGTA, and 1 mM GTP, pH 6.6) to have a final concentration of 10 µM. Tubulin assembly is monitored by fluorescence on 96 well plates according to the method of Barron et al. (Anal. Biochem. 315 (2003) 49-56). To the solution of tubulin (10 µM, 100 µL per well) is added the inhibitor (DMSO, 1 µL) and the solution is incubated for 45 min at room temperature. GTP (1 mM final) is next added, the solution is rapidly mixed and the fluorescence ($\lambda$ex=350 nm, $\lambda$em=440 nm) is measured on a Wallac Victor fluorimeter (Perkin Elmer). The determination of the inhibition of 50% of the maximum assembly rate ($IC_{50}$) is carried out in duplicate or triplicate over 10 concentrations surrounding the $IC_{50}$.

The results are reported in table 2 below.

TABLE 2

Cytotoxicity results on the HCT116 line and inhibition of tubulin polymerisation inhibition (TPI) of the compounds according to the invention.

| | Compound | | | |
| --- | --- | --- | --- | --- |
| | 1 | 2 | 6 | 15 |
| $IC_{50}$ (HCT116) (nM) | 0.07 ± 0.09 | 12 ± 0.8 | 21.6 ± 0.71 | 50.6 ± 0.66 |
| $IC_{50}$ (TPI) (µM) | 1.13 ± 0.16 | 1.40 ± 0.51 | 1.48 ± 0.52 | 1.24 ± 0.40 |

| | Compound | | | |
| --- | --- | --- | --- | --- |
| | 16 | 17 | 18 | 19 |
| $IC_{50}$ (HCT116) (nM) | 24.5 ± 1.92 | 16.7 ± 0.38 | 2.00 ± 0.04 | 0.72 ± 0.03 |
| $IC_{50}$ (TPI) (µM) | 5.76 ± 1.47 | 1.16 ± 0.31 | 1.34 ± 0.45 | 2.78 ± 1.14 |

| | Compound | | | |
| --- | --- | --- | --- | --- |
| | 20 | 9 | 10 | 21 |
| $IC_{50}$ (HCT116) (nM) | 3.28 ± 0.18 | 2.4 ± 0.2 | 1.06 ± 0.2 | 0.20 ± 0.01 |
| $IC_{50}$ (TPI) (µM) | 2.50 ± 0.54 | 3.8 ± 0.9 | 3.14 ± 1.04 | 1.19 ± 0.28 |

| | Compound 14 |
| --- | --- |
| $IC_{50}$ (HCT116) (nM) | 2.88 ± 1.54 |
| $IC_{50}$ (TPI) (µM) | 2.76 ± 0.5 |

2.3. Analysis of the Cell Cycle

The HCT116 cells are seeded in 6 well culture plates at a rate of 300,000 cells per well in their respective media described above. After 24 hours of culture, compound 1 was added to each of the wells at different concentrations. After 24 hours of incubation, the cells are collected individually in 15 mL tubes then centrifuged. The cells are next washed twice in cold PBS then re-suspended in 1 mL of PBS, fixed by adding 2 mL of cold absolute ethanol and placed at 4° C. for 1 hour. After centrifugation, the cells are washed twice in PBS then the cell pellet is taken up in 100 µL of 1%. Triton X100. After 30 minutes of incubation at room temperature, 50 µL of RNase A boiled beforehand (1 mg/mL) and 500 µL of propidium iodide (50 µg/mL) are added to each tube and incubated in darkness at room temperature for 30 minutes. The distribution of the number of cells in each of the phases of the cell cycle is next determined by flow cytometry using a FC500 type cytometer (Beckman-Coulter, France).

Flow cytometry analysis of HCT116 cells treated with compound 1 showed that the latter blocks cellular division in the G2/M phase. This effect is significant after 24 hours of exposure of the cells to compound 1 used at the concentration of 5 nM (FIG. 1).

2.4. Apoptosis

In order to clarify whether compound 1 brings about cell death by apoptosis, the intracellular enzymatic activity of caspases 3 and 7 was evaluated in cultures of HCT116 cells exposed for 24 hours to the action of compound 1.

Apoptosis is measured using the "Apo-one homogeneous caspase-3/7 assay" kit (Promega Co, WI, USA) following the manufacturer's recommendations. Briefly, the cells are seeded in 96 well culture plates at a rate of 50,000 cells per well in 100 µL of culture medium. After 24 hours of incubation, the medium is replaced by 100 µL of culture medium containing different concentrations of compound 1 or 0.1% of DMSO (negative control). After 24 hours of treatment, to each well is added 100 µL of reagent containing the caspase substrate and the buffer for the reaction. After 1 hour incubation, the fluorescence emitted by the cells is measured at 527 nm using a Victor type microplate reader (Perkin-Elmer, USA).

Figure 2:
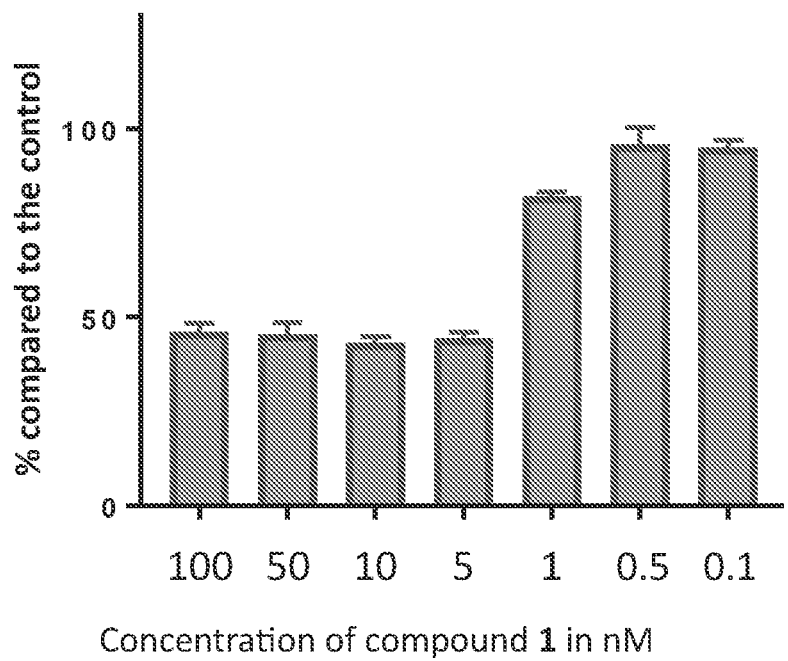
FIG. 2 represents the induction of apoptosis in HCT116 cells treated for 24 h with 1 at various concentrations in DMSO. Apoptosis is demonstrated by the measurement of the enzymatic activity of the caspases 3 and 7 and the results are expressed in % compared to cells treated for 24 h with 0.1% DMSO (control).
Figure 3:
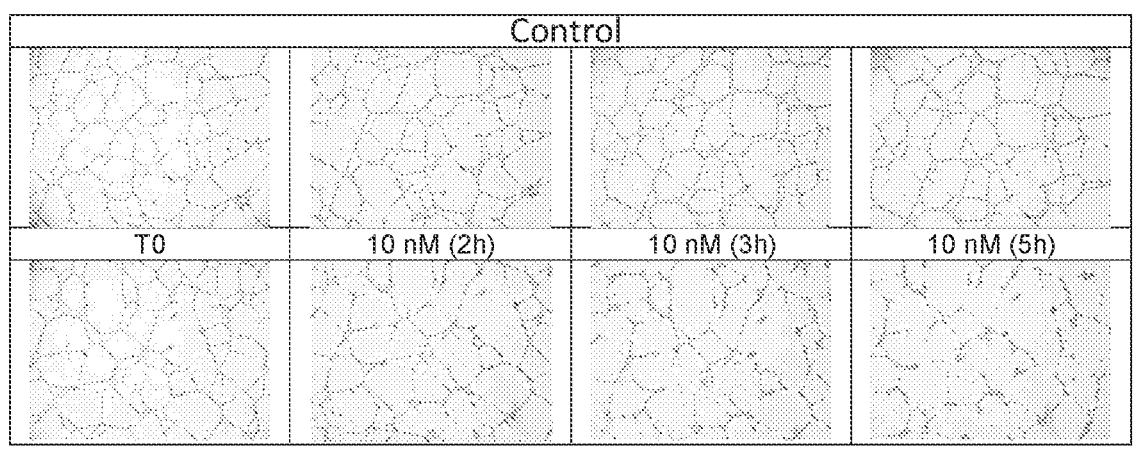
FIG. 3 represents the evolution over time (at t=0 h, t=2 h, t=3 h and t=5 h) of vascular tubes formed by HUVECs fixed on Matrigel in the presence of DMSO (control) or in the presence of compound 1 at a concentration of 10 nM in DMSO.

The results presented in FIG. 2 show that the incubation of the different cells with compound 1 leads to strong induction of apoptosis.

2.5. In Vitro Study on the Formation of Vascular Tubes on Matrigel®

To determine whether compound 1 disrupts the spatial organisation of endothelial cells into structures similar to vascular capillaries, human endothelial cells (HUVECs) were treated immediately after culturing on Matrigel™ or after 24 hours of culture, in order to allow them to form vascular tubes.

The HUVECs (human endothelial cells derived from the umbilical cord) were cultivated in EGM2 culture medium (Promocell, Germany). The cells were maintained in culture at 37° C. in a humid atmosphere containing 5% $CO_2$.

To evaluate the anti-vascular activity of compound 1, the HUVECs were cultured in 96 well culture plates covered beforehand with an extract of extracellular matrix (Matrigel™, BD Biosciences, Le Pont-de-Claix, France) in which they spontaneously form capillary tubes.

Firstly, we measured the capacity of compound 1 to inhibit the formation of the capillary network. Matrigel™ is deposited in the 96 well culture plates at a rate of 70 µL/well and left to incubate at 37° C. for 45 minutes to enable its polymerisation. 20,000 HUVECs are seeded in each of the wells containing Matrigel™ in the absence or in the presence of different concentrations of compound 1, at a rate of 3 wells per concentration. After 2 hours, 3 hours and 5 hours of incubation at 37° C., the cells are observed and photographed using a TE2000 type optical microscope (Nikon, France), equipped with a camera.

In parallel, 20,000 HUVECs were seeded in each of the wells containing Matrigel™. After 16 hours of incubation, when the capillary network is well formed, compound 1 was added at different concentrations. The effect of the product was observed after 2 hours, 3 hours and 5 hours of incubation using an optical microscope.

It may be observed that after treatment of 5 hours at a dose of 10 nM (non-toxic), compound 1 induces a very important decrease in the number of vascular tubes. These results indicate that compound 1 also has an anti-vascular activity potentially useful in therapeutics.

2.6. In Vitro Antigen Presentation Test

The mouse fibrosarcoma line MCA205 was cultivated at 37° C. under 5% $CO_2$ in RPMI-1640 completed with 10% of foetal calf serum (FCS), 1% L-glutamine, 1% penicillin/streptomycin, 1 mM sodium pyruvate and 1% of non-essential amino acids (MEM non-essential amino acids, Gibco). B3Z cells, CD8+ T cell hybridomas, were cultivated at 37° C. under 5% $CO_2$ in RPMI-1640 completed with 10% of foetal calf serum (FCS), 1% L-glutamine, 1% penicillin/streptomycin and 50 µM β-mercaptoethanol. The mouse melanoma line B16F10 was cultivated at 37° C. under 5% $CO_2$ in DMEM containing 10% foetal calf serum (FCS), 1% L-glutamine and 1% penicillin/streptomycin.

The day preceding transfection, the MCA205 were transferred into a 6 well plate at a rate of $1.7.10^5$ cells/well. The B16F10 were transferred into a 6 well plate at a rate of $1.8.10^5$ cells/well. The MCA205 were transfected with 1 µg of plasmid (pcDNA3 or Globin-Intron SL8 representing the antigen sequence being able to be recognised on the cellular surface of the cells expressing it by B3Z hybridomas) using the jetPRIME reagent according to the instructions given by the supplier (Polyplus). The B16F10 were transfected with 1 µg of plasmid (pcDNA3 or Globin-Intron SL8) using GeneJuice the reagent according to the instructions given by the supplier (Novagen).

The different compounds diluted in DMSO were added 24 h after transfection for 18 h. Thereafter, 50,000 transfected cells (MCA205 or B16F10) were cultured in the presence of 100,000 B3Z cells in a 96 well plate for 18 h. The peptide SIINFEKL was added at 1 µg/well as control. After 5 minutes of centrifugation at 1200 rpm, the cells were washed twice with 200 µL of PBS, then lysated in 50 µL of lyse buffer (0.2% TritonX-100, 10 mM DL-Dithiothreitol (Sigma), 90 mM $K_2HPO_4$ and 8.5 mM $KH_2PO_4$ in water). After 10 min of centrifugation at 3000 rpm, 45 µL of supernatant were transferred into a white opaque 96 well plate (OptiPlaque-96, PerkinElmer). 100 µL of revelation buffer (10 mM $MgCl_2$, 11.2 mM β-mercaptoethanol, 0.0015% IGEPAL® CA-630 and 40 µM 4-Methylumbelliferyl β-D-Galactopyranoside (MUG) in PBS) were added to each well for an incubation of at least 3 h protected from light. The β-galactosidase activity of the B3Z is measured by fluorescence on a FLUOstar Optima (BMG Labtech). The excitation filter is programmed at 355 nm, that of emission at 460 nm.

Figure 4:
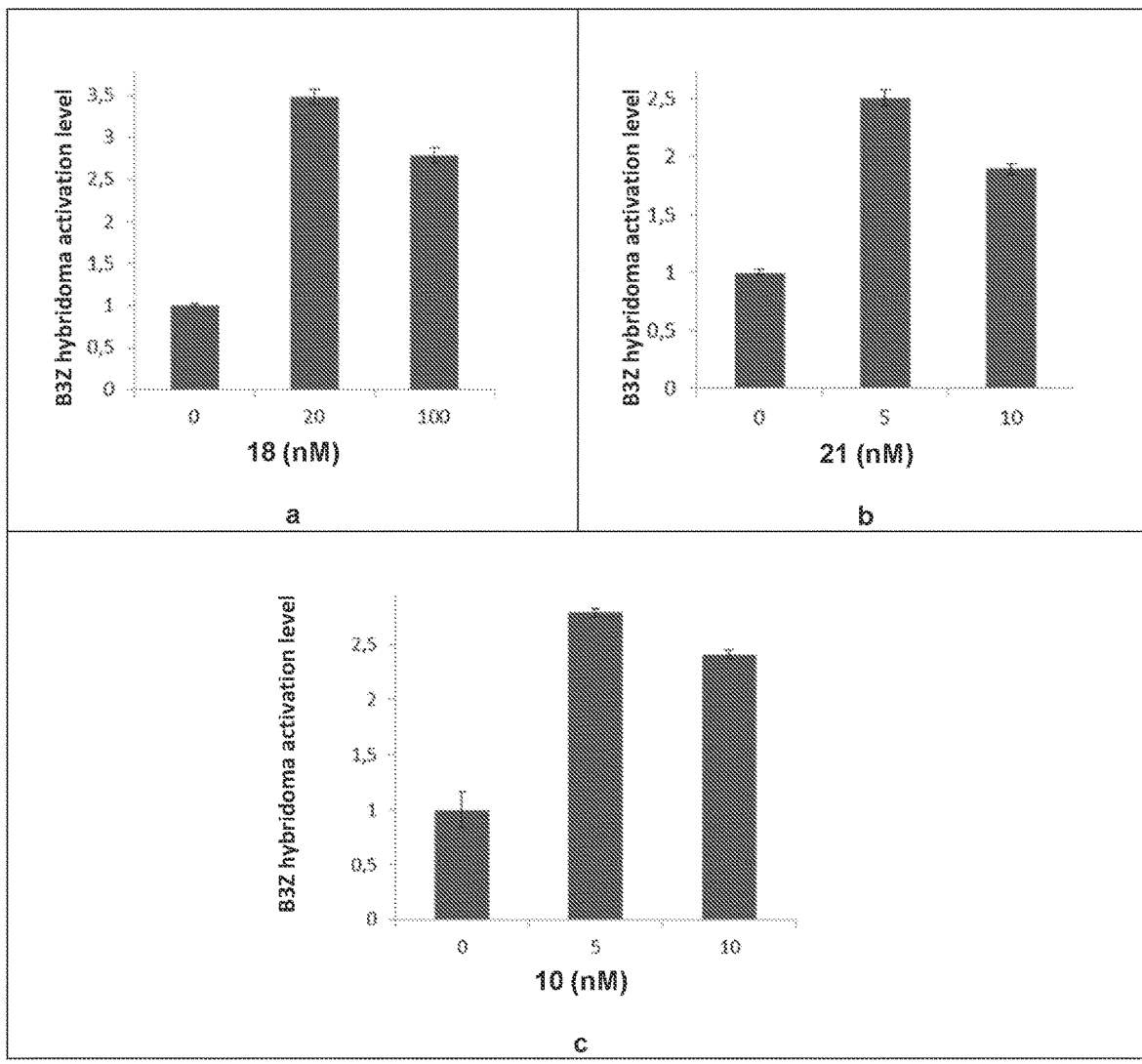
FIG. 4 represents the variation in antigen presentation to CD8 T lymphocytes in the MCA205 sarcoma line as a function of the concentration of compound 18 (FIG. 4a), 21 (FIG. 4b) and 10 (FIG. 4c).

The variation in antigen presentation in the MCA205 sarcoma line is represented in FIG. 4: as a function of the concentration of compound 18 (FIG. 4a), 21 (FIG. 4b) and 10 (FIG. 4c).

Figure 5:
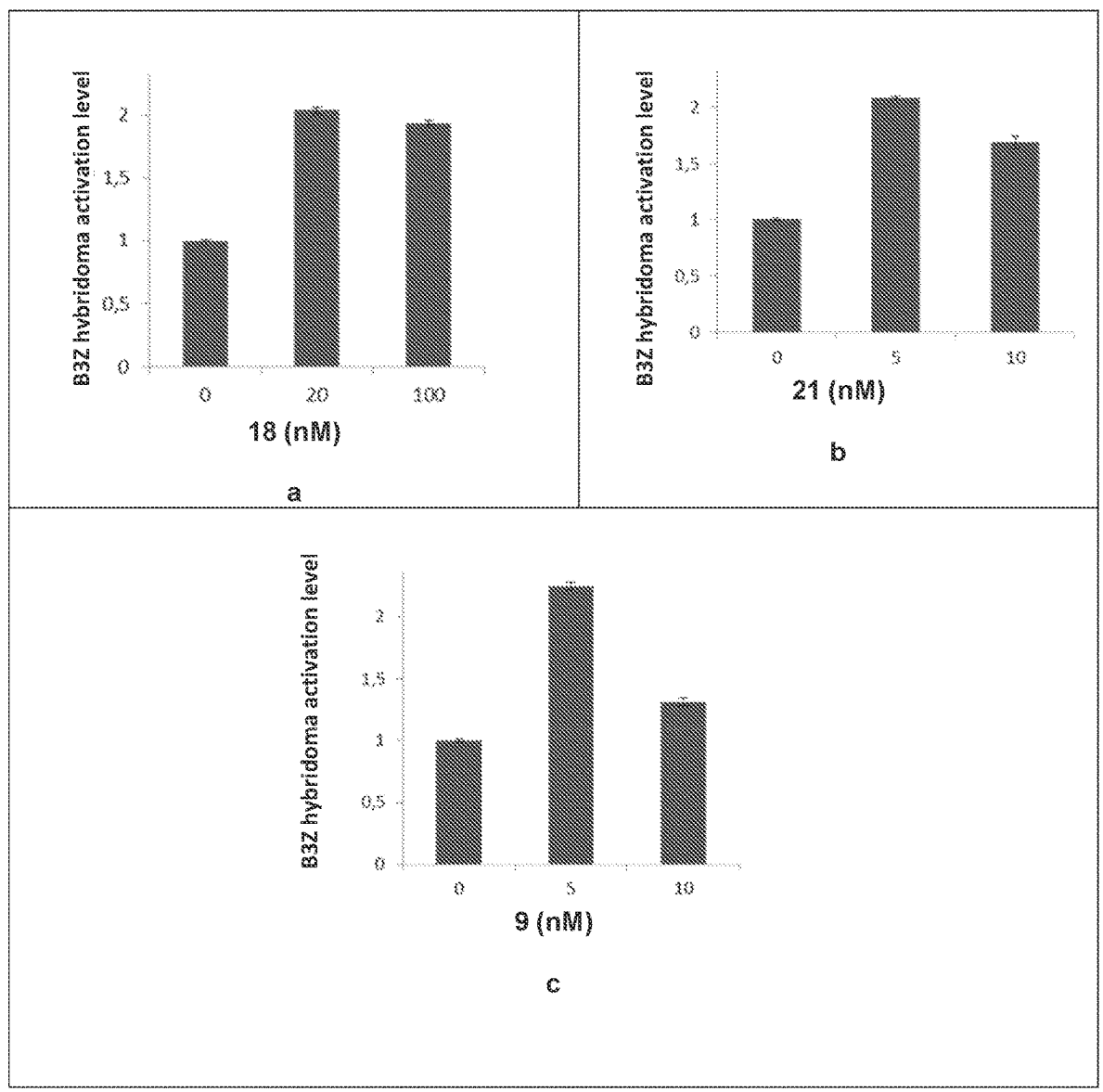
FIG. 5 represents the antigen presentation in the B16F10 melanoma line as a function of the concentration of compound 18 (FIG. 5a), 21 (FIG. 5b) and 9 (FIG. 5c).

The variation in antigen presentation in the B16F10 melanoma line is represented in FIG. 5: as a function of the concentration of compound 18 (FIG. 5a), 21 (FIG. 5b) and 9 (FIG. 5c).

The invention claimed is:

1. A method for treating cancer comprising the administration to a patient in need thereof of an effective quantity of a compound of following formula (I):

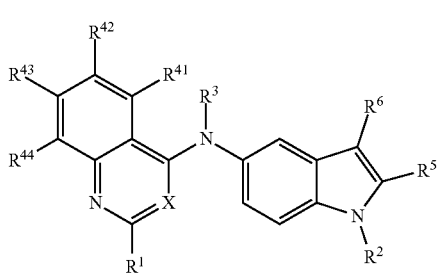

in which:
- X represents a —CH— group or a nitrogen atom,
- $R^1$ represents a hydrogen atom, a halogen atom, a $(C_1-C_6)$alkyl group, a —CN group or a —CF$_3$ group,
- $R^2$ represents a hydrogen atom, a $(C_1-C_6)$alkyl group, an aryl-$(C_1-C_6)$alkyl group, or a —COR$^{21}$ group with $R^{21}$ representing a $(C_1-C_6)$alkyl group or an aryl group,
- $R^3$ represents a $(C_1-C_6)$alkyl group, an aryl-$(C_1-C_6)$ alkyl group or a —COR$^{31}$ group with $R^{31}$ representing a $(C_1-C_6)$alkyl group or an aryl group,
- $R^{41}$, $R^{42}$, $R^{43}$ and $R^{44}$ represent independently of each other a hydrogen atom; a halogen atom; —OR$^{45}$; —SR$^{45}$; —NR$^{45}$R$^{46}$; —NO$_2$; or a $(C_1-C_6)$alkyl group optionally substituted by one or more substituents selected from among a halogen atom, —OR$^{45}$, —SR$^{45}$, —NR$^{45}$R$^{46}$ and —NO$_2$, with $R^{45}$ and $R^{46}$ representing independently of each other a hydrogen atom, a $(C_1-C_6)$alkyl group, a —CF$_3$ group or a —COR$^{47}$ group with $R^{47}$ representing a $(C_1-C_6)$alkyl group or an aryl group,
- $R^5$ and $R^6$ represent a hydrogen atom or form together a —CR$^{51}$=CR$^{52}$—CR$^{53}$=CR$^{54}$— chain with $R^{51}$, $R^{52}$, $R^{53}$ and $R^{54}$ representing independently of each other a hydrogen atom; a halogen atom; —OR$^{55}$; —SR$^{55}$; —NR$^{55}$R$^{56}$; —NO$_2$; or a $(C_1-C_6)$alkyl group optionally substituted by one or more substituents selected from among a halogen atom, —OR$^{55}$, —SR$^{55}$, —NR$^{55}$R$^{56}$ and —NO$_2$, with $R^{55}$ and $R^{56}$ representing independently of each other a hydrogen atom, a $(C_1-C_6)$alkyl group, a —CF$_3$ group or a —COR$^{57}$ group with $R^{57}$ representing a $(C_1-C_6)$alkyl group or an aryl group,
- wherein, when X represents a nitrogen atom, $R^1$ represents a chlorine atom, a —CN group or a —CF$_3$ group, or $R^5$ and $R^6$ form together a —CR$^{51}$=CR$^{52}$—CR$^{53}$=CR$^{54}$— chain, or a pharmaceutically acceptable salt thereof, wherein the cancer is selected from colorectal carcinoma, ovarian cancer, pancreatic cancer, K562R Doxorubicin resistant chronic myeloid leukaemia, and JIM-T1 Trastuzumab-DM1 resistant mammal carcinoma.

2. The method according to claim 1, wherein $R^1$ represents a chlorine atom, a —CN group or a —CF$_3$ group.

3. The method according to claim 1, wherein $R^1$ represents a chlorine atom.

4. The method according to claim 1, wherein $R^3$ represents a $(C_1-C_6)$alkyl group and/or $R^2$ represents a $(C_1-C_6)$ alkyl group, or an aryl-$(C_1-C_6)$alkyl group.

5. The method according to claim 4, wherein $R^3$ represents a methyl group.

6. The method according to claim 4, wherein $R^2$ represents a methyl group or a benzyl group.

7. The method according to claim 4, wherein $R^2$ represents a methyl group.

8. The method according to claim 1, wherein $R^{41}$, $R^{42}$, $R^{43}$ and $R^{44}$ represent independently of each other a hydrogen atom, a halogen atom, —OR$^{45}$, —SR$^{45}$, —NR$^{45}$R$^{46}$ or —NO$_2$ with $R^{45}$ and $R^{46}$ representing independently of each other a hydrogen atom, a CF$_3$ group or a $(C_1-C_6)$alkyl group.

9. The method according to claim 8, wherein $R^{41}$, $R^{42}$, $R^{43}$ and $R^{44}$ represent independently of each other a hydrogen atom, —OR$^{45}$, —NR$^{45}$R$^{46}$ or —NO$_2$ with $R^{45}$ and $R^{46}$ representing independently of each other a hydrogen atom, or a $(C_1-C_6)$alkyl group.

10. The method according to claim 8, wherein $R^{41}$, $R^{42}$, $R^{43}$ and $R^{44}$ represent a hydrogen atom.

11. The method according to claim 1, wherein the compound of formula (I) is a compound of following formula (Ia):

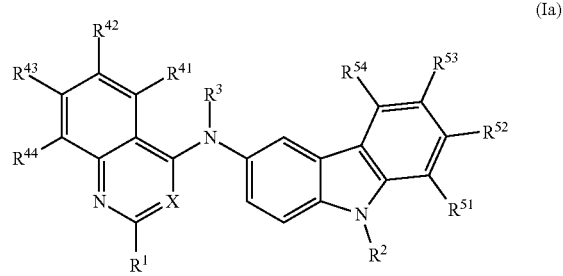

in which X, $R^1$, $R^2$, $R^3$, $R^{41}$, $R^{42}$, $R^{43}$, $R^{44}$, $R^{51}$, $R^{52}$, $R^{53}$ and $R^{54}$ are as defined in claim 1, or a pharmaceutically acceptable salt thereof.

12. The method according to claim 1, wherein $R^{51}$, $R^{52}$, $R^{53}$ and $R^{54}$ represent independently of each other a hydrogen atom, —OR$^{55}$, —NR$^{55}$R$^{56}$, —NO$_2$ or a $(C_1-C_6)$alkyl group optionally substituted by one or more substituents selected from among a halogen atom, a —OR$^{55}$, —SR$^{55}$, —NR$^{55}$R$^{56}$ and —NO$_2$ group, with $R^{55}$ and $R^{56}$ representing independently of each other a hydrogen atom or a $(C_1-C_6)$ alkyl group.

13. The method according to claim 1, wherein $R^{51}$, $R^{52}$, $R^{53}$ and $R^{54}$ represent independently of each other a hydrogen atom, a halogen atom, —OR$^{55}$, —NR$^{55}$R$^{56}$, —NO$_2$ or a $(C_1-C_6)$alkyl group optionally substituted by a —OR$^{55}$ group, with $R^{55}$ and $R^{56}$ representing independently of each other a hydrogen atom, a CF$_3$ group or a $(C_1-C_6)$alkyl group.

14. The method according to claim 1, wherein $R^5$ and $R^6$ represent a hydrogen atom.

15. The method according to claim 1, wherein the compound of formula (I) is a compound of following formula (Ib):

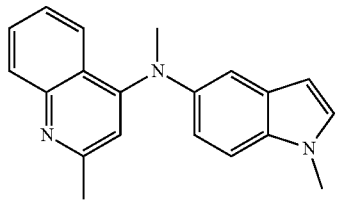
(Ib)
or a pharmaceutically acceptable salt thereof.
16. The method according to claim 1, wherein the compound of formula (I) is selected from among:
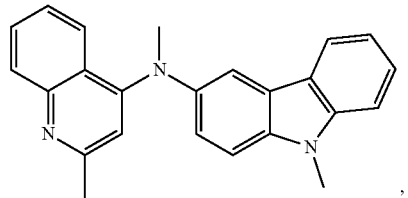,
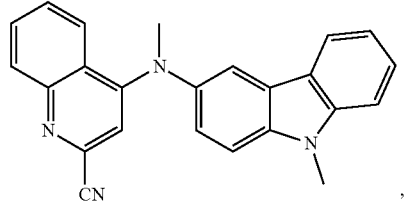,
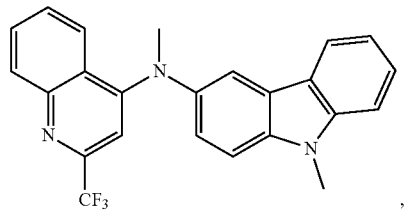,
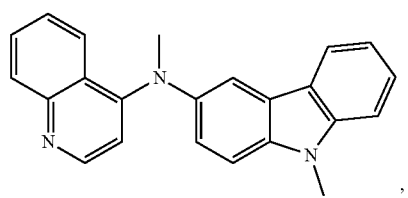,
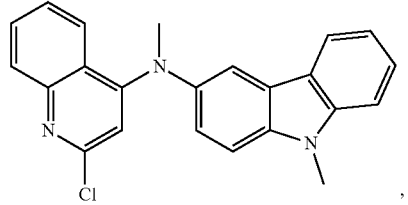,
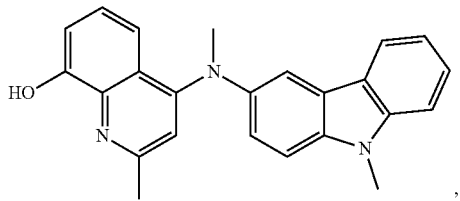,
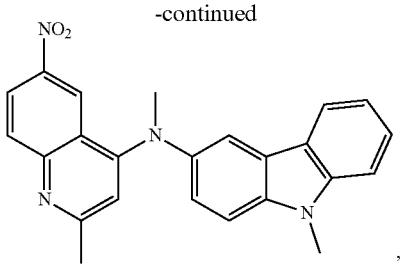,
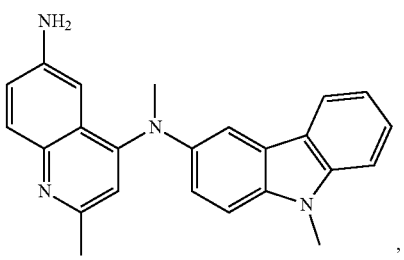,
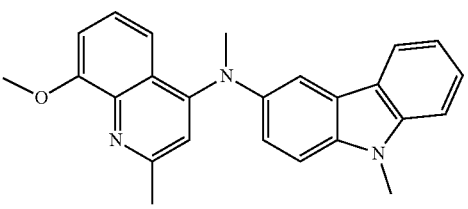,
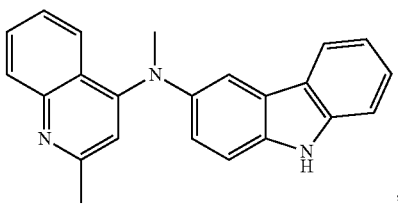,
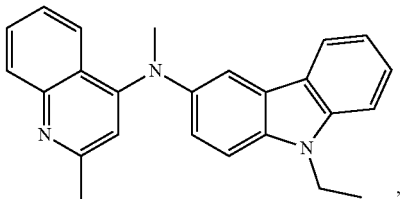,
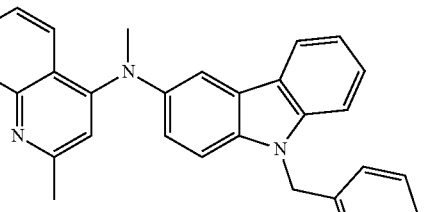,
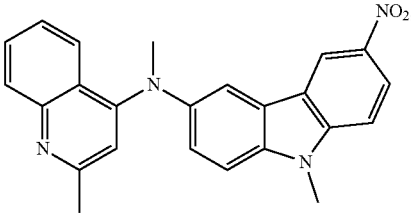,

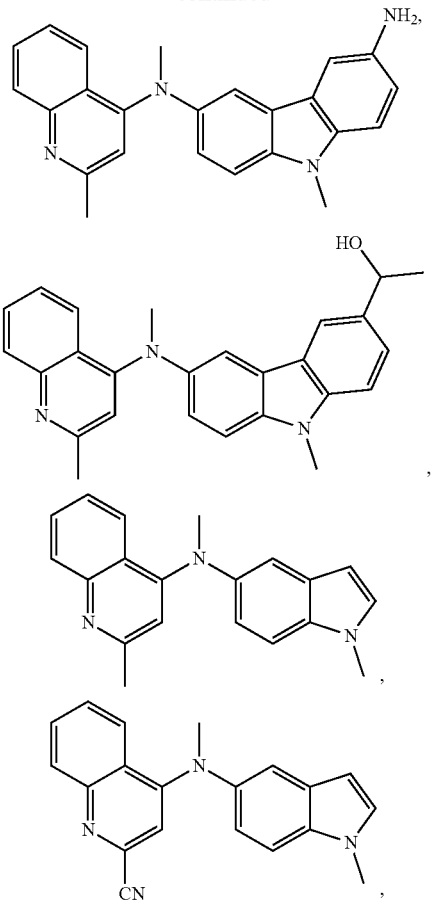
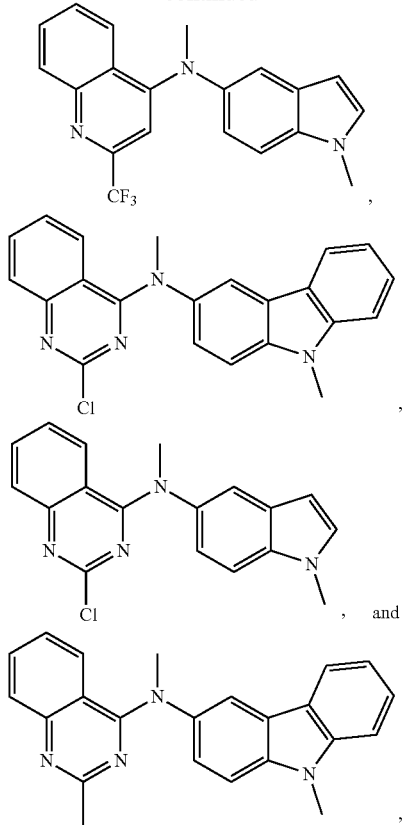
and pharmaceutically acceptable salts thereof.
* * * * *